United States Patent
Stolowitz et al.

[11] Patent Number: 5,831,045
[45] Date of Patent: Nov. 3, 1998

[54] BORONIC ACID-CONTAINING POLYNUCLEOTIDES

[75] Inventors: Mark L. Stolowitz, Woodinville; Robert J. Kaiser, Bothell, both of Wash.

[73] Assignee: Porlinx, Incorporated, Bothell, Wash.

[21] Appl. No.: 834,001

[22] Filed: Apr. 11, 1997

Related U.S. Application Data

[62] Division of Ser. No. 692,429, Aug. 5, 1996.

[51] Int. Cl.$^6$ .......................... C07H 19/00; C07H 21/04; C12Q 1/68
[52] U.S. Cl. ........................... 536/22.1; 435/6; 536/24.3; 536/27.1; 536/27.11; 536/27.13
[58] Field of Search ............................ 435/6; 536/22.1, 536/24.3, 27.1, 27.11, 27.13

[56] References Cited

U.S. PATENT DOCUMENTS

| | | |
|---|---|---|
| 4,711,955 | 12/1987 | Ward . |
| 5,241,060 | 8/1993 | Engelhardt . |
| 5,328,824 | 7/1994 | Ward . |
| 5,449,767 | 9/1995 | Ward . |
| 5,466,679 | 11/1995 | Soloway et al. .......................... 514/50 |
| 5,476,928 | 12/1995 | Ward . |
| 5,594,111 | 1/1997 | Stolowitz . |
| 5,594,151 | 1/1997 | Stolowitz . |

OTHER PUBLICATIONS

Yamamoto et al. "Boron–10 for NCT. A new synthetic method via condensation with aldehydes having boronic moiety" *Tetrahedron Letters*, vol. 30, No. 51, pp. 7191–7194, 1989.
Langer, et al. (1981) *Proc. Natl. Acad. Sci USA* 78:6633–6637.
Kessler, et al. (1980) *Biol. Chem. Hoppe–Seyler* 371:917–965.
Krichta, ed. (1992) *Nonisotopic DNA Probe Techniques*, Academic Press, Chapter 1.
Kessler, ed. (1995) *Nonisotopic Probing, Blotting, and Sequencing*, Academic Press, Chapter 2.
Singhal, et al. (1992) *Adv. Chromatog.* 31:293–335.
Mazzeo, et al. (1989) *BioChromatog.* 4:124–130.
Bergold, et al. (1983), in *Solid Phase Biochemistry*, Scouten, ed., John Wiley & Sons, New York, pp. 149–187.
Mertes, et al. (1970) *J. Heterocyclic Chem.* 1:751.
Deschamps, et al. (1978) *J. Med. Chem.* 21:228.
Hashimoto, et al. (1993) *J. Org. Chem.* 58:4194–4195.
Hashimoto, et al. (1993) *J. Am. Chem. Soc.* 115:7128–7134.
Linder, et al. (1991) *Bioconjugate Chem.* 2:160–170.
Linder, et al. (1991) *Bioconjugate Chem.* 2:407–415.
Dale, et al. (1973) *Proc. Natl. Acad. Sci. USA* 70:2238.
Dale, et al. (1975) *Biochemistry* 14:2447.
Feinberg, et al. (1988) *Anal. Biochem.* 132:6–13.
Abhay, et al. (1988) *Anal. Biochem.* 169:376–382.
Weith, et al. (1970) *Biochemistry* 9:4396–4401.
Ho, et al. (1981) *Biochemistry* 20:64–67.
Yamanmoto et al. "Boron–10 carriers for NCT. A new synthetic method via condensation with aldehydes having boronic moiety", *Tetrahedron Letters*, vol. 30, No. 51, pp. 7791–7194.

*Primary Examiner*—Ardin H. Marschel
*Assistant Examiner*—Jezia Riley
*Attorney, Agent, or Firm*—Townsend and Townsend and Crew LLP

[57] ABSTRACT

Modified nucleotides and polynucleotides which are useful in hybridization assays for the detection of target genes are provided. The modified polynucleotides contain at least one boronic acid moiety which is attached to a nucleotide base in a position which does not interfere with the hydrogen bonding capabilities of that base during duplex formation. The modified polynucleotides are typically formed from naturally occurring nucleotides and one or more modified nucleotides.

5 Claims, 21 Drawing Sheets

PBA-XX-dUTP

COMPLEX $X^2$ = OH, $NH_2$, NHR, NHOH, NHOR
(R IS LOWER ALKYL)

$Y^2$ = O, S, OR NH $Z^2$ IS, FOR EXAMPLE,

OR

THE SUBSCRIPTS n, m, j AND k EACH REPRESENT INTEGERS OF FROM 1 TO 6

LABELED COMPLEX ($Y^2$ = O, $X^2$ = NHOR)

STEP 1

STEP 2

STEP 3

STEP 4

STEP 1

STEP 2

STEP 3

STEP 4

STEP 5

STEP 1

STEP 2

STEP 3

STEP 4

STEP 5

STEP 1

STEP 2

STEP 3

STEP 4

STEP 1

Bz = $CH_2C_6H_5$

STEP 2

STEP 3

STEP 4

STEP 5

1 dTTP Control
2 dTTP after DHBHA-Sepharose
3 3:1 PBA-XX-dUTP/dTTP
4 3:1 PBA-XX-dUPT/dTTP after DHBHA-Sepharose
5 3:1 PBA-X-dUTP/dTTP
6 3:1 PBA-X-dUTP/dTTP after DHBHA-Sepharose
7 5:1 PBA-XX-dUTP/dTTP
8 5:1 PBA-XX-dUTP/dTTP after DHBHA-Sepharose 1  1Kb Ladder
2  PBA-XX-dUTP
3  dTTP
4  3:1 PBA-XX-dUTP/dTTP
5  3:1 PBA-X-dUTP/dTTP
6  5:1 PBA-XX-dUTP/dTTP
7  5:1 PBA-X-dUTP/dTTP
8  10:1 PBA-XX-dUTP/dTTP
9  10:1 PBA-X-dUTP/dTTP
10 dTTP with PBA-Primer 1 dTTP Control 2 dTTP after DHBHA-Sepharose 3 PBA-XX-dUTP Control 4 PBA-XX-dUTP after DHBHA-Sepharose 5 1Kb Ladder

BORONIC ACID-CONTAINING POLYNUCLEOTIDES

This is a Division of application Ser. No. 08/692,429 filed Aug. 5, 1996, the disclosure of which is incorporated by reference.

CROSS-REFERENCE TO RELATED APPLICATIONS

This application is related to applications U.S. Ser. Nos. 08/188,460, 08/188,531, 08/188,958 and 08/188,176, each of which was filed on Jan. 28, 1994 and is incorporated herein by reference. This application is also related to copending applications U.S. Ser. Nos. 08/689,341; 08/691,929; 08/691,930; 08/689,283, which were filed Aug. 5, 1996 as continuations-in-part of one or more of the above applications.

FIELD OF THE INVENTION

The present invention relates to the field of gene probe detection, and particularly to modified polynucleotides which are useful in the detection of target genes.

BACKGROUND OF THE INVENTION

Nucleic acid hybridization tests for the detection of specific DNA and RNA sequences are now common in research and are becoming common in diagnostic applications. These hybridization tests typically involve the use of a labeled nucleic acid probe in such assay formats as dot blots, Southern blots, Northern blots, in situ hybridization, plaque hybridization and colony hybridization. A variety of labels have been used in these assays including, for example, radiolabels, chemiluminescent compounds, enzymes and fluorescent compounds.

Almost as diverse as the labels are the methods of attaching the label to the nucleic acid probe. Briefly, the attachment of labels to a nucleic acid probe can be accomplished by either direct or indirect methods. Direct labeling is the result of attaching a label to a nucleic acid probe via a covalent linkage, typically prior to formation of a duplex. Alternatively, the label can be incorporated noncovalently into a duplex via intercalation. For indirect labeling, a hapten is attached to the nucleic acid probe, and later detected using a labeled specific binding protein.

One example of an indirect labeling system is the biotin-streptavidin system described in Langer, et al., *Proc. Natl. Acad. Sci. USA* 78:6633–6637 (1981), the disclosure of which is incorporated herein by reference. In this system, a biotin moiety is attached to a nucleic acid probe and detection is carried out using a labeled avidin or labeled streptavidin. Methods for the attachment of biotin to the 5-position of a pyrimidine (e.g., uridine), the 8-position of a purine (e.g., guanidine) and the 7-position of a deazapurine (e.g., 7-deazaguanidine) have been described in U.S. Pat. Nos. 4,711,955, 5,241,060, 5,328,824, 5,449,767 and 5,476,928, each of which is incorporated herein by reference. While the biotin system is characterized by high sensitivity, an endogenous ubiquitous vitamin, vitamin H, is used as the modification group. This results in extraneous background signals, especially with biological samples.

Another indirect method involves the use of the hapten digoxigenin (see, Kessler, et al., *Biol. Chem. Hoppe-Seyler* 371:917–965 (1990)). This system uses the digoxigenin and antibody fragments derived from sheep polyclonal antibodies against digoxigenin. This method is also characterized by subpicogram sensitivity, and circumvents the problem of extraneous background signal by using the cardenolide digoxigenin which occurs only in Digitalis plants. Nevertheless, digoxigenin is an expensive reagent.

What is needed in the art are new methods of indirect labeling of probe:nucleic acid hybrids which have broad applicability, do not suffer from extraneous background signals and which provide modified duplexes which can be rapidly purified by affinity methods. Surprisingly, the present invention provides such methods, as well as the monomers and modified nucleic acids which are employed therein.

SUMMARY OF THE INVENTION

The present invention provides modified polynucleosides and polynucleotides which are useful in hybridization assays for the detection of target genes. The modified polynucleotides contain at least one boronic acid moiety which is attached to a nucleotide base in a position which does not interfere with the hydrogen bonding capabilities of that base during duplex formation. The modified polynucleotides are typically formed from naturally occurring nucleotides and one or more modified nucleotides having the formula:

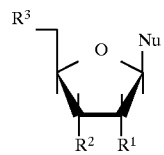

in which $R^1$, $R^2$ and $R^3$ are each independently hydrogen, hydroxyl, protected hydroxyl, monophosphate ester, diphosphate ester, or triphosphate ester; Nu is a radical such as

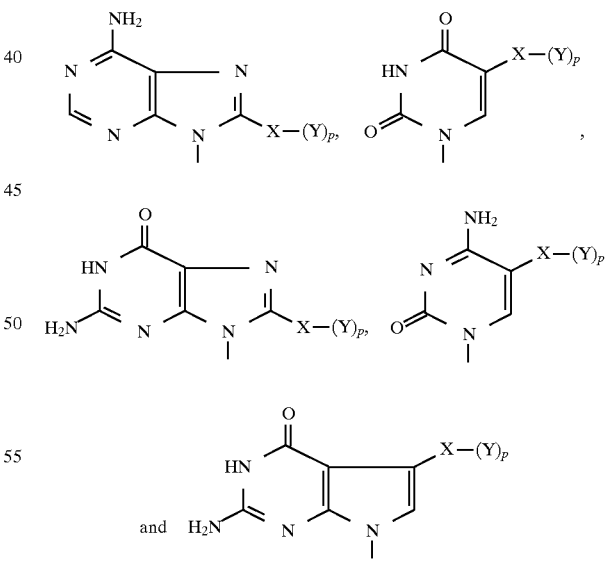

in which X is a linking group having from 7 to 30 carbon atoms, a portion of which is an aromatic ring; Y is a boron-containing moiety, preferably a boronic acid or boronic ester; and p is an integer of from 1 to 3.

The present invention further provides modified polynucleosides and polynucleotides having the formula:

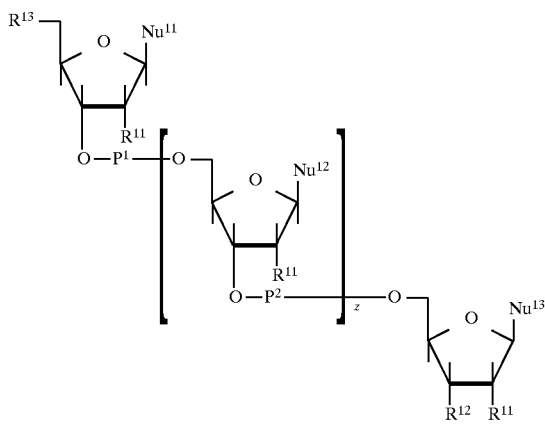

in which z is an integer of from 1 to 1000; each $R^{11}$ is independently —H or —OH; each $R^{12}$ and $R^{13}$ is independently hydroxyl, protected hydroxyl, monophosphate ester, diphosphate ester, or triphosphate ester; each $P^1$ and $P^2$ is independently —P(O)(OH)—, —P(O)(NH$_2$)—, —P(S)(OH)—, —P(O)(CH$_3$)—, or a pharmaceutically acceptable salt thereof; each $Nu^{11}$, $Nu^{12}$ and $Nu^{13}$ is independently

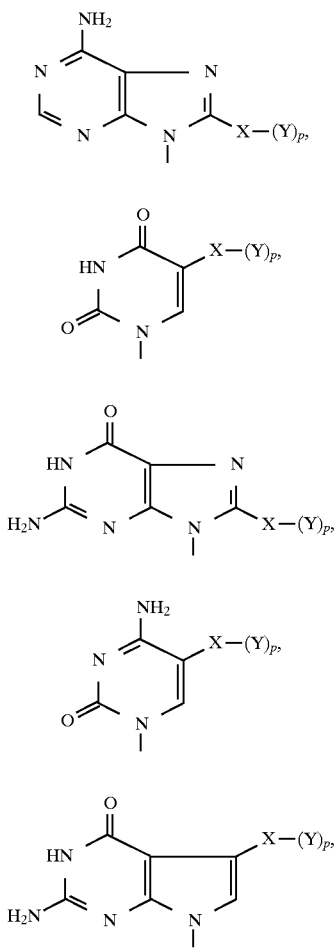

in which X is a linking group of from 7 to 30 carbon atoms, a portion of which is an aromatic ring; Y is a boron-containing moiety, prefereably a boronic acid or boronic ester moiety; and p is an integer of from 1 to 3. For the above polynucleotides, at least one and no more than thirty of $Nu^{11}$, $Nu^{12}$ and $Nu^{13}$ are other than adenine, guanine, thymine or cytosine.

Still further, the present invention provides methods for the use of the modified polynucleotides and related derivatives to detect the presence of target nucleic acids in a sample.

BRIEF DESCRIPTION OF THE DRAWINGS

FIG. 4 illustrates the use of modified polynucleotides in target polynucleotide detection.

DETAILED DESCRIPTION OF THE INVENTION

Abbreviations

Figure 1:
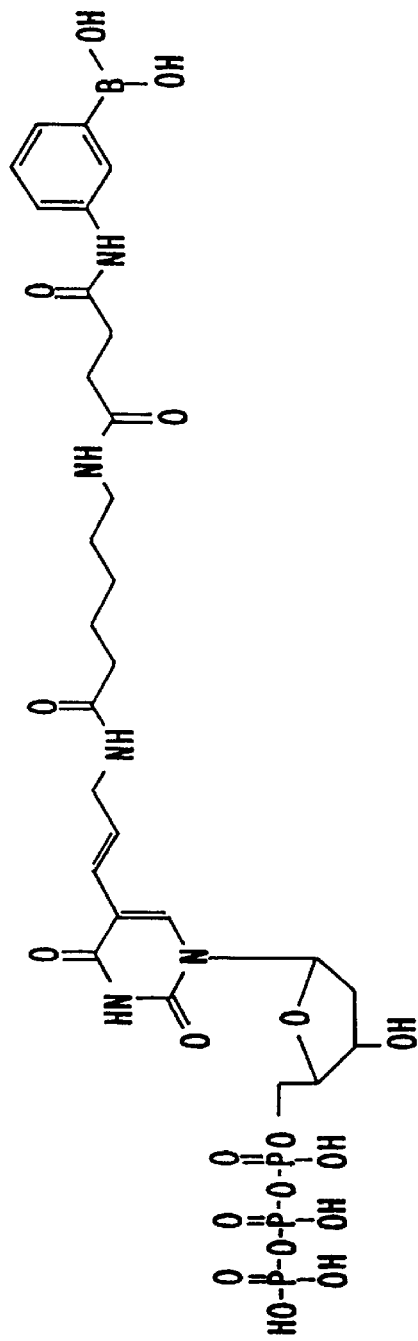
FIG. 1 illustrates the structure of PBA-XX-dUTP and also illustrates a complex which is formed with a boronic acid complexing reagent.
Figure 1:
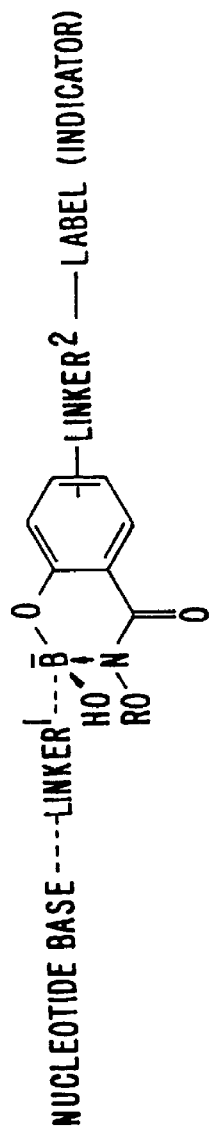

The following abbreviations are used herein: AA, amino allyl; PBA, phenylboronic acid; SHA, salicylhydroxamic acid; DHBHA, 2,6-dihydroxybenzo-hydroxamic acid; PCR, polymerase chain reaction; NHS, N-hydroxysuccinimide; PBA-XX-dUTP, 5-(3-aminophenylboronicacidsuccinamidohexanoyl)-aminoallyldeoxy-uridine5'-triphosphate; PBA-X-dUTP, 5-(3-aminophenylboronicacid succinamido)allyldeoxy-uridine5'-triphosphate.

Description of the Embodiments

The field of nucleic acid probes has been the subject of several recent reviews. See, NONISOTOPIC DNA PROBE TECHNIQUES, Academic Press, Chapter 1, Krichta, ed. (1992) and NONISOTOPIC PROBING, BLOTTING, AND SEQUENCING, Academic Press, Chapter 2, Kessler, ed. (1995), each of which is incorporated herein by reference.

The present invention provides modified nucleic acid monomers which are useful for the preparation of modified polynucleotides. These polynucleotides find application in nucleic acid detection methods described more fully below. The modified nucleic acid monomers will contain a boric or boronic acid moiety attached to the heterocyclic portion of the nucleic acid. The attachment is made via a linking group which is typically from 7 to 30 carbon atoms in length, contains an aromatic ring and is optionally interrupted by one or more amide, ester, disulfide, urea, carbamate, hydrazone, ether, thioether, amine or imine groups. As used herein, the term "aromatic ring" is meant to include both carbocyclic and heterocyclic aromatic rings such as, for example, a phenyl, naphthyl, thienyl, furanyl or pyrazolyl ring. The linking group will also be of sufficient length that the boronic acid group can form a complex with a boronic acid complexing agent when the modified nucleic acid is incorporated into an polynucleotide. The term "polynucleotide" refers to a single or double-stranded polymer of deoxyribonucleotide or ribonucleotide bases read from the 5' to the 3' end. It includes both self-replicating plasmids, infectious polymers of DNA or RNA and non-functional DNA or RNA.

Modified polynucleotides are also provided in which the polynucleotide is constructed from naturally-occurring monomeric nucleic acids and one or more modified nucleic acid monomers of the present invention. The modified polynucleotides of the present invention will typically be from 10 to 1000 bases in length and contain from 1 to about 30 modified monomers. The number of modified monomers should not be so great as to interfere with the intended purpose of the polynucleotide.

Boronic acid and boronate ester moieties form complexes with certain polar molecules and have been exploited in a number of chromatographic methods. In these methods, a boronic acid group is immobilized on a solid support and used to selectively retain those polar molecules having the required functionality which includes 1,2-diols, 1,3-diols, 1,2-hydroxyacids, 1,3-hydroxyacids, 1,2- and 1,3-hydroxylamines, and 1,2- and 1,3-diketones. Each of these functional groups are known to form complexes with, for example, phenylboronic acid. Additionally, these functional groups are present in a number of biological molecules including carbohydrates, catecholamines, prostaglandins, ribonucleosides and steroids. The use of boronic acid chromatographic media for the isolation and separation of biological molecules has been reviewed. See, Singhal, et al., *Adv. Chromatog.* 31:293–335 (1992); Mazzeo, et al., *Bio-Chromatog.* 4:124–130 (1989); and Bergold, et al., in SOLID PHASE BIOCHEMISTRY, Scouten, ed., John Wiley & Sons, New York, pp. 149–187 (1983).

Boric or boronic acids are Lewis acids and ionize by hydration in which the trigonal acid is converted to a tetrahedral boronate anion. Similarly, when complexes are formed with a boronic acid, the boron adopts a tetrahedral configuration in which the average bonds lengths to the boron atom are about 10% longer. More importantly, complexes are formed in a pH dependent manner in many instances. See, Lorand, et al., *J. Org. Chem.* 24:769 (1959), Sienkiewicz, et al., *J. Inorg. Nucl. Chem.*, 42:1559–1571 (1980) and Tanner, et al., *J. Am. Chem. Soc.* 89:6954 (1967). This property provides additional advantages for the use of boronic acids in the monomers, polynucleotides and methods described below.

Boron-Containing Monomers

In one aspect, the present invention provides modified nucleic acids having the formula:

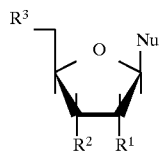

In this formula, $R^1$, $R^2$ and $R^3$ are each independently hydrogen, hydroxyl, protected hydroxyl, monophosphate ester, diphosphate ester, or triphosphate ester. In preferred embodiments, $R^1$ is hydrogen, hydroxyl or protected hydroxyl; $R^2$ is hydroxyl, protected hydroxyl, or monophosphate ester; and $R^3$ is hydroxyl, protected hydroxyl, monophosphate ester, diphosphate ester, or triphosphate ester. The symbol Nu represents a radical which is:

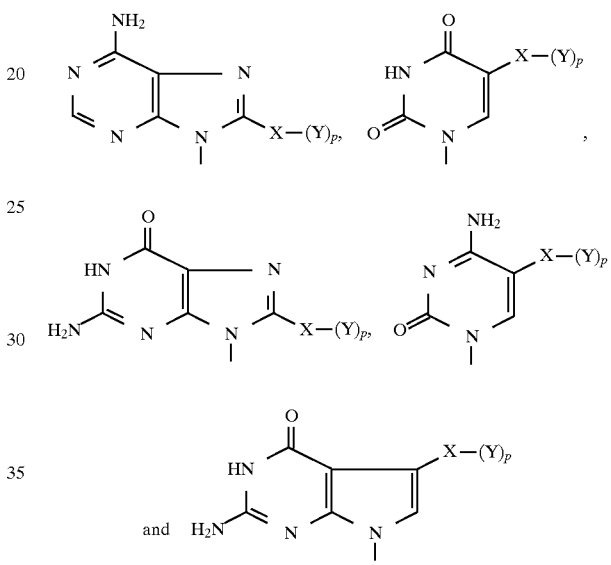

in which the letter X represents a linking group of from 7 to 30 carbon atoms, at least a portion of which is an aromatic ring. The linking group is optionally interrupted by one or more amide, ester, disulfide, urea, carbamate, hydrazone, ether, thioether, amine or imine groups. The letter Y represents a boron-containing moiety which is typically a boronic acid, a borinic acid, or a boronic acid ester. Examples of such groups are —B(OH)$_2$, —B(OH)(OR) and —B(OR)(OR') in which R and R' are alkyl groups of from 1 to 6 carbon atoms which, in some embodiments, can be linked together to form a cyclic ester. The letter p represents an integer of from 1 to 3.

The linking groups used in this aspect of the invention will typically comprise of from 7 to 30 carbon atoms. In preferred embodiments, the linking group is an alkylene chain which is interrupted by one or more amide, ether, thioether, dissulfide, ester, thioester, urea and amine linkages and terminates in an aromatic ring. Examples of such linkages include —CH═CH—CH$_2$—NHCOAr—, —CH═CH—CH$_2$—NHAr—, —CH═CH—CH$_2$—O—Ar—, —CH═CH—CONH—Ar—, —CH═CH—CH$_2$—CONH—Ar—, —CH═CH—CH$_2$—NHCO—(CH$_2$)$_n$—NHCO—Ar—, and —CH═CH—CH$_2$—NHCO—(CH$_2$)$_n$—NHCO—(CH$_2$)$_m$—CONH—Ar— in which Ar represents a divalent aromatic ring which is phenyl or naphthyl and n and m independently represent integers of from 1 to 6. More preferably, X is

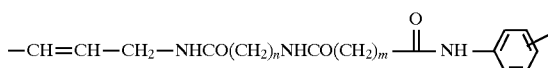

and n and m independently represent integers of from 1 to 6. One of skill in the art will understand that while the above preferred linkages all contain a site of unsaturation adjacent to the nucleic acid portion of the monomer, the invention is not so limited. The requirements for X are more simply that X does not interfere with duplex formation when the monomers are incorporated into polynucleotides and that X provide sufficient clearance for the boronic acid or ester moiety (Y) to engage in binding of complexing agents without affecting duplex stability for polynucleotides containing the above monomers.

In one group of embodiments, —X— and —(Y)$_p$ are taken together and comprise a radical which is

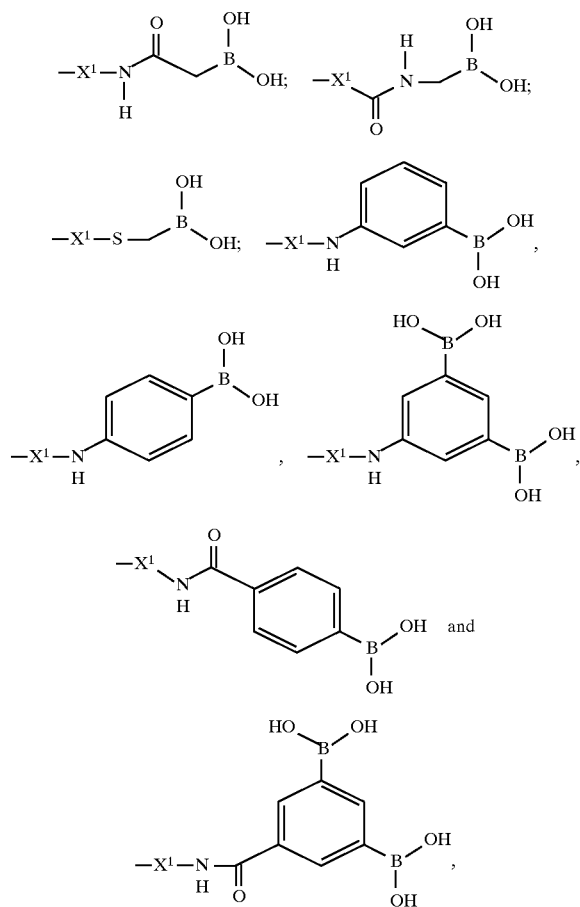

in which $X^1$ is a linking group fragment having from 3 to 23 carbon atoms. In preferred embodiments, the linking group fragment is —CH=CH—(CH$_2$)$_n$—NHCO—, —CH=CH—(CH$_2$)$_m$—, —CH=CH—(CH$_2$)$_m$—O—, —CH=CH—CONH—, —CH=CH—(CH$_2$)$_n$—CO—, —CH=CH—CH$_2$—NHCO—(CH$_2$)$_n$—NHCO—, and —CH=CH—CH$_2$—NHCO—(CH$_2$)$_n$—NHCO—(CH$_2$)$_m$—CO— in which n and m independently represent integers of from 1 to 6.

The monomers in this aspect of the present invention can be prepared by a number of methods. For the preparation of modified pyrimidine bases (e.g. modified uridines and cytidines), a synthetic scheme is preferred which begins with the preparation of 5-aminoallyl-dUTP (see, Langer, et al., *Proc. Natl. Acad. Sci. USA*, 78:6633–6637 (1981), incorporated herein by reference). Briefly, deoxyuridine 5'-triphosphate is first chloromercurated at the 5-position using mercuric chloride, then treated with allylamine in the presence of potassium tetrachloropalladate to effect a carbon-carbon bond formation and provide 5-aminoallyl-dUTP. Alternatively, the same procedures can be employed with, for example, deoxyuridine, deoxyuridine 5'-monophosphate, deoxyuridine 5'-diphosphate, uridine 5'-triphosphate, uridine 5'-diphosphate, uridine 5'-monophosphate, uridine, and the corresponding cytidine compounds.

In other embodiments, the modified nucleic acids can be prepared beginning with 5-hydroxymethyl-2'-deoxycytidine monophosphate (prepared by enzymatic hydrolysis of non-glycosylated phage T$_4$DNA as described in U.S. Pat. No. 5,241,060, incorporated herein by reference), 5-(4-aminobutylaminomethyl)-2'-deoxyuridinemonophosphate (see U.S. Pat. No. 5,241,060), 5-formyl-2'-deoxyuridine (see, Mertes, et al., *J. Heterocyclic Chem.* 1:751 (1970), incorporated herein by reference), and 5-(oxy)acetic acid-2'-deoxyuridine (see, Deschamps, et al., *J. Med. Chem.* 21:228 (1978), incorporated herein by reference).

Figure 2:
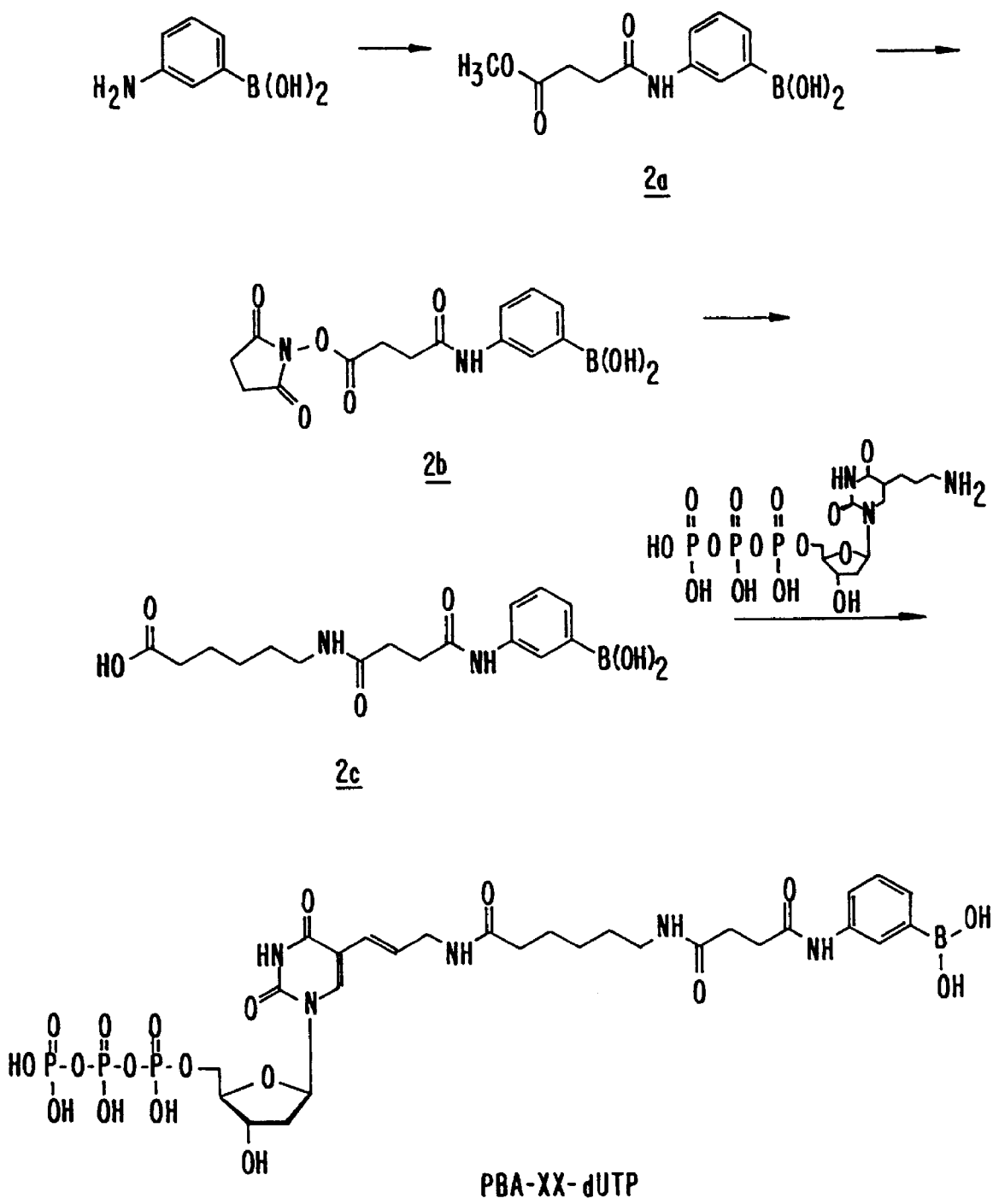
FIG. 2 illustrates a synthesis scheme for the preparation of PBA-XX-dUTP.

Following the addition of a functional group at the 5-position, the linker can be extended and a suitable boronic acid group can be appended. Alternatively, a more convergent approach can be taken in which the desired boronic acid or boronic acid-containing moiety is attached to a portion of the linking group and the resulting combination is then attached to the 5-aminoallyl-dUTP. FIG. 2 provides a synthetic scheme for the preparation of PBA-XX-dUTP. In this scheme, 3-aminophenylboronic acid is treated with methyl succinyl chloride to provide the amide 2a. Subsequent saponification of the ester and coupling of the activating group N-hydroxysuccinimide (NHS) provides the activated ester 2b. Treatment of 2b with 6-aminohexanoic acid provides 2c which can be coupled with 5-aminoallyl-dUTP to provide the monomer depicted in FIG. 1 (abbreviated as PBA-XX-dUTP).

Alternatively, modified nucleic acids can be prepared using synthetic methods described in Hashimoto, et al., *J. Org. Chem.* 58:4194–4195 (1993) and Hashimoto, et al., *J. Am. Chem. Soc.* 115:7128–7134 (1993), incorporated herein by reference. Briefly, modified uridine and cytidine analogs are synthesized beginning with the corresponding 5-iodo-2'-deoxyuridine and 5-iodo-2'-deoxycytidine. Reaction of the iodo-nucleosides with an appropriately protected amino alkyne in the presence of a palladium catalyst provides the desired carbon framework for further elaboration. Hydrogenation of the newly introduced alkyne can be accomplished over a palladium on carbon catalyst to provide analogs having a protected amine which is linked to the nucleotide via a saturated carbon tether. In other embodiments the alkyne may kept as part of the linking group or may be reduced to an alkene using controlled hydrogenation over palladium on carbon catalysts. The remaining steps for elongation of the linking group and attachment of a boronic acid moiety will follow those steps described above.

One of skill in the art will understand that similar synthetic methodologies can be used which begin with other boronic acid-containing species, for example, (4-carboxyphenyl)boronic acid, (3-isothiocyanatophenyl) boronic acid, (3-iodoacetamidophenyl)boronic acid, (5-carboxy-3-isothiocyanatophenyl)boronic acid and (3-maleimidophenyl)-boronic acid. These compounds are either commercially available or can be prepared by methods described in Linder, et al., *Bioconjugate Chem.*

Figure 3:
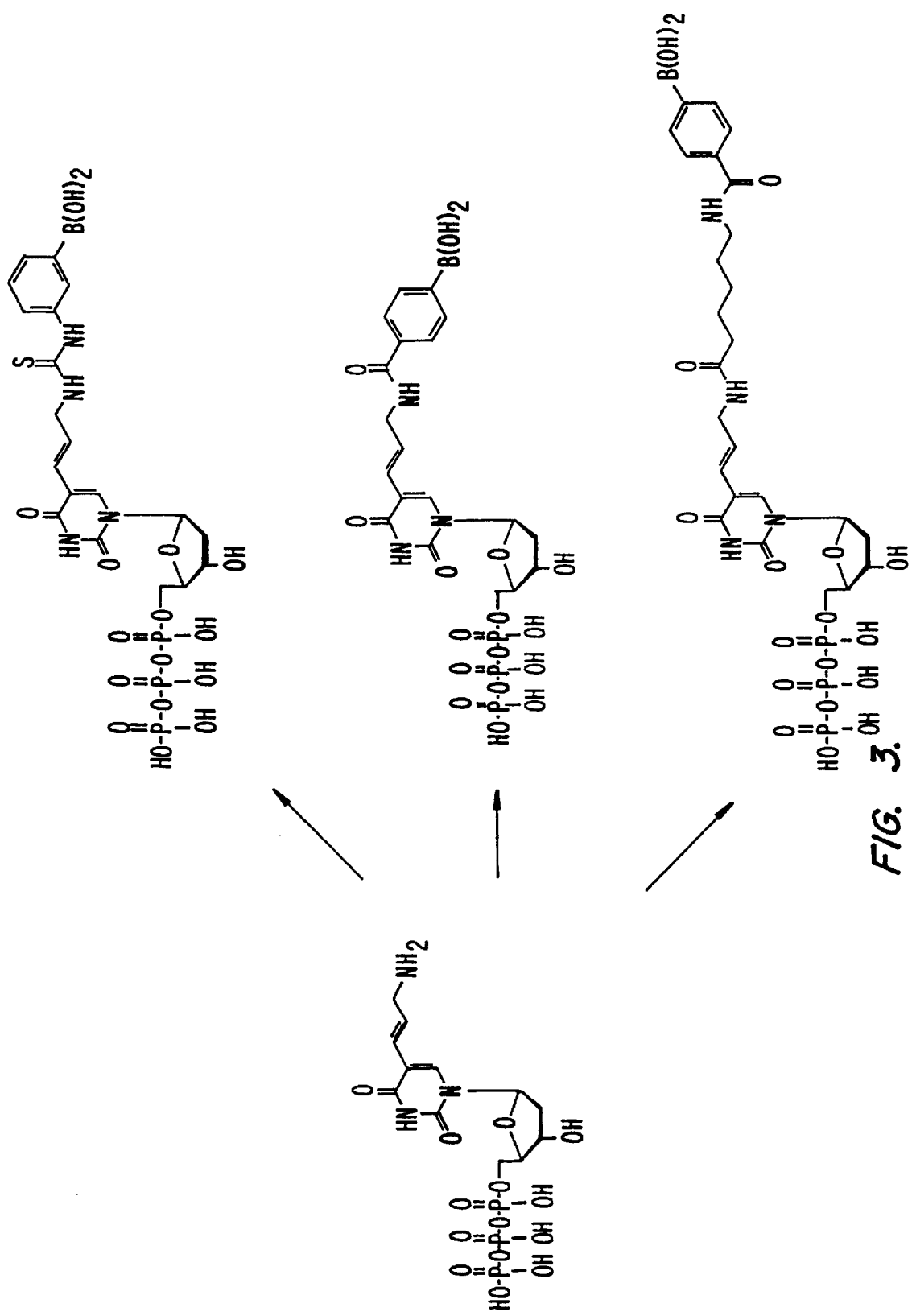
FIG. 3 illustrates alternative coupling reactions beginning with 5-aminoallyl-dUTP.

2:160–170 (1991) or Linder, et al., *Bioconjugate Chem.* 2:407–415 (1991), each of which is incorporated herein by reference. Examples of suitable derivatization and coupling to 5-aminoallyl-dUTP are provided in FIG. 3. The general synthetic methods provided in FIGS. 2 and 3 all utilize 5-aminoallyl-dUTP as the acceptor for the boronic acid-containing group. However, one of skill in the art will appreciate that other suitably substituted nucleic acids could be used as well (e.g., the commercially available N6-(aminohexyl)-dATP.

Preparation of modified purine nucleotides and deazapurine nucleotides can also be carried out as described above for pyrimidine nucleosides. Mercuration of the C8 position of the purine ring and the C7 position of a deazapurine has been described. See, Dale, et al., *Proc. Natl. Acad. Sci. USA* 70:2238 (1973) and Dale, et al., *Biochemistry* 14:2447 (1975), the disclosures of which are incorporated herein by reference. Following mercuration of the nucleosides, allyl amine can be coupled to the heterocyclic ring using the procedures outlined above. Further synthesis to provide the monomers of the present invention are then be carried out, also as described above.

Boron-Containing Polynucleotides

In another aspect, the present invention provides modified polynucleotides having the formula:

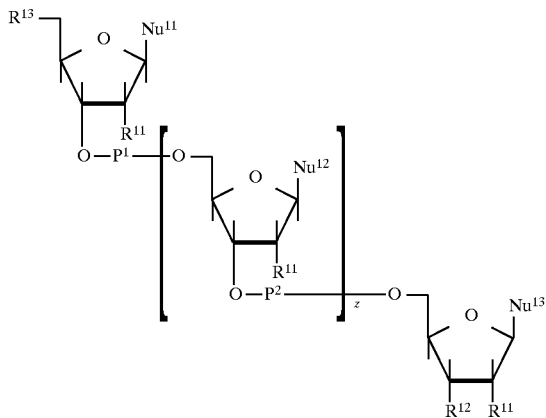

In this formula, z represents an integer of from 1 to 1000 and each $R^{11}$ is —H or —OH. The symbols $R^{12}$ and $R^{13}$ each independently represent a hydroxyl, protected hydroxyl, monophosphate ester, diphosphate ester, or triphosphate ester. The symbols $P^1$ and $P^2$ are each independently —P(O)(OH)—, —P(O)(NH$_2$)—, —P(S)(OH)—, —P(O)(CH$_3$)—, or a pharmaceutically acceptable salt thereof.

In the above formula, each $Nu^{11}$, $Nu^{12}$ and $Nu^{13}$ is independently adenine, guanine, thymine, cytosine or a modified nucleic acid base having the formula:

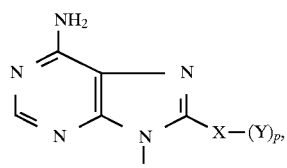

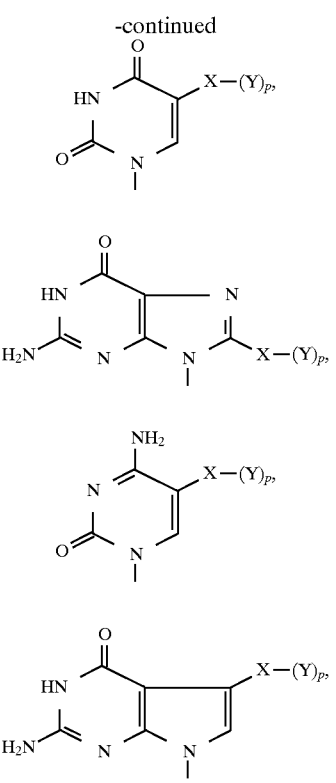

The nucleic acid derivatives above, are modified to have a boron-containing moiety which is attached to the heterocyclic ring portion by means of a linking group X. Typically, the linking group comprises of from 7 to 30 carbon atoms, a portion of which is present as an aromatic ring. Preferred groups for X are those which have been described above for the monomers of the present invention. The boron-containing moiety, Y, is a boronic acid substituent such as —B(OH)$_2$, —B(OH)(OR) and —B(OR)(OR') in which R and R' are alkyl groups of from 1 to 6 carbon atoms which, in some embodiments, can be linked together to form a cyclic ester. As used herein, the term "alkyl" refers to a saturated hydrocarbon radical which may be straight-chain or branched-chain (for example, ethyl, isopropyl, t-amyl, or 2-methylpentyl). Preferred groups for Y are also those which have been described above for the monomers. The modified polynucleosides and polynucleotides of the present invention are constructed such that at least one and no more than thirty of $Nu^{11}$, $Nu^{12}$ and $Nu^{13}$ are other than adenine, guanine, thymine or cytosine. One of skill in the art will understand that the number of modified nucleic acid monomers in an polynucleotide will depend in part on the particular application (e.g., the sensitivity of the complexing agent which is ultimately attached to the boronic acid moiety in various assays). Additionally, the modified monomers should not be so numerous as to interfere with the intended purpose of the modified polynucleotide (e.g., binding or duplex formation with a target gene or target polynucleotide). Thus, for example, an polymer of 20 to 30 monomers will typically contain from one to five modified monomers, while an polymer of 1000 monomers can contain up to about 30 modified monomers.

Preparation of Boron-Containing Polynucleotides

The boron-containing polynucleotides used in the present invention may be synthesized in solid phase or in solution, using the above boron-containing monomers and other nucleoside bases. In some embodiments, the boron-containing polynucleotides are prepared using enzyme-based methodology such as PCR, random prime labeling, tailing or nick translation.

Alternatively, polynucleotide synthesis can be carried out using commercially available monomers such as, for example, N6-(6-aminohexyl)-dATP. After the polynucleotide has been prepared, one or more boronic acid-containing moieties can be attached to the pendent amino group using methods described above and in the examples which follow.

Solid phase synthesis

Detailed descriptions of the procedures for solid phase synthesis of polynucleotides by phosphite-triester, phosphotriester, and H-phosphonate chemistries are widely available. See, for example, Itakura, U.S. Pat. No. 4,401, 796; Caruthers, et al., U.S. Pat. Nos. 4,458,066 and 4,500, 707; Beaucage, et al., Tetrahedron Lett., 22:1859–1862 (1981); Matteucci, et al., J. Am. Chem. Soc., 103:3185–3191 (1981); Caruthers, et al., Genetic Engineering, 4:1–17 (1982); Jones, chapter 2, Atkinson, et al., chapter 3, and Sproat, et al., chapter 4, in Oligonucleotide Synthesis: A Practical Approach, Gait (ed.), IRL Press, Washington D.C. (1984); Froehler, et al., Tetrahedron Let., 27:469–472 (1986); Froehler, et al., Nucleic Acids Res., 14:5399–5407 (1986); Sinha, et al. Tetrahedron Lett., 24:5843–5846 (1983); and Sinha, et al., Nucl. Acids Res., 12:4539–4557 (1984) which are incorporated herein by reference.

Generally, the timing of delivery and concentration of monomeric nucleotides utilized in a coupling cycle will not differ from the protocols typical for commercial phosphoramidites used in commercial DNA synthesizers. In these cases, one may merely add the solution containing the monomers to a receptacle on a port provided for an extra phosphoramidite on a commercial synthesizer (e.g., model 380B, Applied Biosystems, Foster City, Calif., U.S.A.). However, where the coupling efficiency of a particular monomer is substantially lower than the other phosphoramidites, it may be necessary to alter the timing of delivery or the concentration of the reagent in order to optimize the synthesis. Means of optimizing polynucleotide synthesis protocols to correct for low coupling efficiencies are well known to those of skill in the art. Generally one merely increases the concentration of the reagent or the amount of the reagent delivered to achieve a higher coupling efficiency. Methods of determining coupling efficiency are also well known. For example, where the 5'-hydroxyl protecting group is dimethoxytrityl (DMT), coupling efficiency may be determined by measuring the DMT cation concentration during the acidic removal of the DMT group. DMT cation concentration is usually determined by spectrophotometrically monitoring the acid wash. The acid/DMT solution is a bright orange color. Alternatively, since capping prevents further extension of an polynucleotide where coupling has failed, coupling efficiency may be estimated by comparing the ratio of truncated to full length polynucleotides utilizing, for example, capillary electrophoresis or HPLC.

Solid phase polynucleotide synthesis may be performed using a number of solid supports. A suitable support is one which provides a functional group for the attachment of a protected monomer which will become the 3' terminal base in the synthesized polynucleotide. The support must be inert to the reagents utilized in the particular synthesis chemistry. Suitable supports are well known to those of skill in the art. Solid support materials include, but are not limited to polyacryloylmorpholide, silica, controlled pore glass (CPG), polystyrene, polystyrene/latex, and carboxyl-functionalized teflon. Preferred supports are amino-functionalized controlled pore glass and carboxylfunctionalized teflon.

Solid phase polynucleotide synthesis requires, as a starting point, a fully protected monomer (e.g., a protected nucleoside) coupled to the solid support. This coupling is typically through the 3'-hydroxyl. Typically, a linker group is covalently bound to the 3'-hydroxyl on one end and covalently bound to the solid support on the other end. The first synthesis cycle then couples a nucleotide monomer, via its 3'-phosphate, to the 5'-hydroxyl of the bound nucleoside through a condensation reaction that forms a 3'-5' phosphodiester linkage. Subsequent synthesis cycles add nucleotide monomers to the 5'-hydroxyl of the last bound nucleotide. In this manner an polynucleotide is synthesized in a 3' to 5' direction producing a "growing" polynucleotide with its 3' terminus attached to the solid support.

Numerous means of linking nucleoside monomers to a solid support are known to those of skill in the art, although monomers covalently linked through a succinate or hemisuccinate to controlled pore glass are generally preferred. Conventional protected nucleosides coupled through a hemisuccinate to controlled pore glass are commercially available from a number of sources (e.g., Glen Research, Sterling, Vt., U.S.A.; Applied Biosystems, Foster City, Calif., U.S.A.; and Pharmacia LKB, Piscataway, N.J., U.S.A.).

Once the full length polynucleotide is synthesized, the polynucleotide is deprotected and cleaved from the solid support prior to use. Cleavage and deprotection may occur simultaneously or sequentially in any order. The two procedures may be interspersed so that some protecting groups are removed from the polynucleotide before it is cleaved off the solid support and other groups are deprotected from the cleaved polynucleotide in solution. The sequence of events depends on the particular blocking groups present, the particular linkage to a solid support, and the preferences of the individuals performing the synthesis. Where deprotection precedes cleavage, the protecting groups may be washed away from the polynucleotide which remains bound on the solid support. Conversely, where deprotection follows cleavage, the removed protecting groups will remain in solution with the polynucleotide. Often the polynucleotide will require isolation from these protecting groups prior to use.

In a preferred embodiment, and most commercial DNA syntheses, the protecting group on the 5'-hydroxyl is removed at the last stage of synthesis. The polynucleotide is then cleaved off the solid support, and the remaining deprotection occurs in solution. Removal of the 5'-hydroxyl protecting group typically requires treatment with the same reagent utilized throughout the synthesis to remove the terminal 5'-hydroxyl protecting groups prior to coupling the next nucleotide monomer. Where the 5'-hydroxyl protecting group is a dimethoxytrityl group, deprotection can be accomplished by treatment with acetic acid, dichloroacetic acid, trichloroacetic acid or trifluoroacetic acid.

Where the polynucleotide is a ribonucleotide and the 2'-hydroxyl group is blocked with a tert-butyldimethylsilyl (TBDMS) moiety, the latter group may be removed using tetrabutylammonium fluoride in tetrahydrofuran at the end of synthesis. See Wu, et al., J. Org. Chem. 55:4717–4724 (1990). Phenoxyacetyl protecting groups can be removed with anhydrous ammonia in alcohol (under these conditions the TBDMS groups are stable and the polynucleotide is not cleaved). The benzoyl protecting group of cytidine is also removed with anhydrous ammonia in alcohol.

Cleaved and fully deprotected polynucleotides may be used directly (after lyophilization or evaporation to remove the deprotection reagent) or they may be purified prior to use. Purification of synthetic polynucleotides is generally desired to isolate the full length polynucleotide from the protecting groups that were removed in the deprotection step and, more importantly, from the truncated polynucleotides that were formed when polynucleotides that failed to couple with the next nucleotide monomer were capped during synthesis.

Polynucleotide purification techniques are well known to those of skill in the art. Methods include, but are not limited to, thin layer chromatography (TLC) on silica plates, gel electrophoresis, size fractionation (e.g., using a Sephadex column), reverse phase high performance liquid chromatography (HPLC) and anion exchange chromatography (e.g., using the mono-Q column, Pharmacia-LKB, Piscataway, N.J. U.S.A.). For a discussion of polynucleotide purification see McLaughlin, et al., chapter 5, and Wu, et al., chapter 6 in *Oligonucleotide Synthesis: A Practical Approach*, Gait (ed.), IRL Press, Washington, D.C., (1984).

Enzyme-Based Methodology

The synthesis of modified polynucleotides containing a modified monomer described above can also be achieved by enzyme-based methods as detailed in the examples set forth below. Pyrimidine, purine and deazapurine nucleoside triphosphates containing a boronic acid moiety linked to the heterocyclic ring can be used as substrates for a wide variety of purified nucleic acid polymerases of both prokaryotic and eukaryotic origin. These include Taq DNA polymerase, DNA polymerase I of *E. coli*, bacteriophage T4 DNA polymerase, DNA polymerases alpha and beta from murine (A-9) and human (HeLa) cells, and the DNA polymerase of Herpes simplex virus. Nick-translation, random prime labeling, and terminal transferase tailing are also useful methods for the incorporation of a modified nucleic acid monomer into an polynucleotide. Nick-translation can be carried out as described in Rigby, et al., *J. Mol. Biol.* 113:237–251 (1977), incorporated herein by reference. Random prime labeling can be conducted utilizing a modification of the method of Feinberg, et al., *Anal. Biochem.* 132:6–13 (1988) in which a modified monomer is used in place of dTTP. Incorporation can be verified by capture of the probe (or modified polynucleotide) on DHBHA-Sepharose. Tailing, or terminal transfer can be carried out using the method of Abhay, et al., *Anal. Biochem.* 169:376–382 (1988) in which a modified (boronic acid-containing) monomer is diluted into dTTP. As above, incorporation of the modified monomer can be verified by capture of the probe on DHBHA-Sepharose.

Methods of Using Boron-Containing Polynucleotides

Figure 4A:
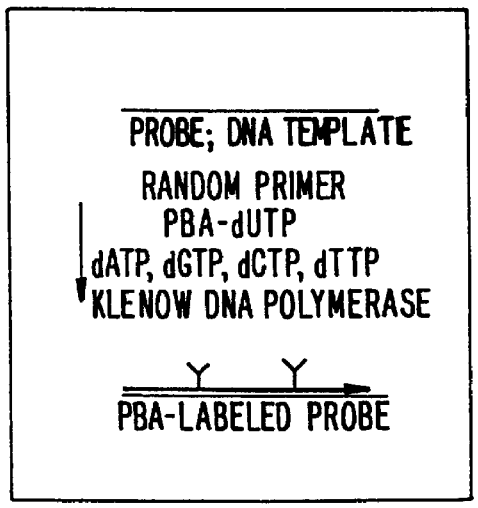
FIG. 4(a) illustrates random-primed DNA labeling.
Figure 4B:
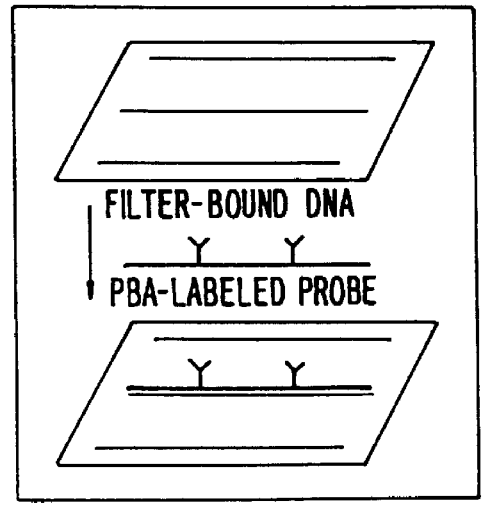
FIG. 4(b) illustrates blot hybridization.
Figure 4C:
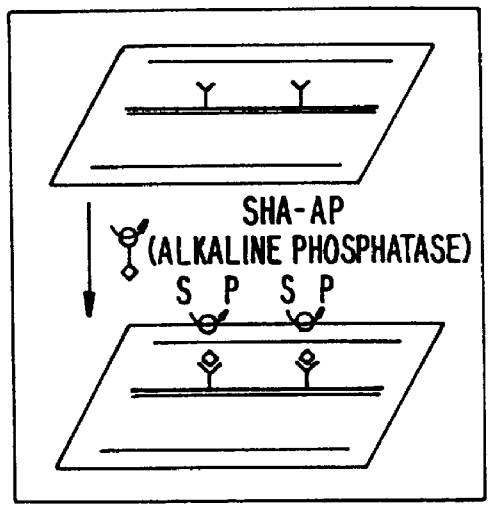
FIG. 4(c) illustrates enzyme-linked detection.

The boron-containing polynucleotides of the present invention have application in numerous diagnostic methods. FIG. 4 illustrates one applications for the use of the modified polynucleotides in a DNA probe detection system. In FIG. 4a, a modified polynucleotide is prepared using random-primed DNA labeling and PBA-XX-dUTP as the boron-containing monomer. One of skill in the art will understand that any of the monomers described above could also be used, as well as alternative methods of polymer formation (e.g., nick translation, solid phase synthesis, and terminal transferase). Following preparation of the PBA-labeled probe, a blot hybridization can be carried out in which the labeled probe is applied to filter-bound DNA (FIG. 4b), under conditions in which hybridization takes place between the probe and a target polynucleotide. The presence of a target polynucleotide can then be determined using, for example, enzyme-linked detection. As shown in FIG. 4c, alkaline phosphatase-linked to a boronic acid complexing moiety such as salicylhydroxamic acid (SHA, represented in FIG. 4c as a diamond shape), will complex to the boronic acid portion of the probe (represented by the "Y" in FIGS. 4a–c). Subsequent treatment with a substrate for alkaline phosphatase which forms a detectable product (S→P, in FIG. 4c) provides a means by which the presence of the target nucleic acid or polynucleotide can be detected.

Figure 5:
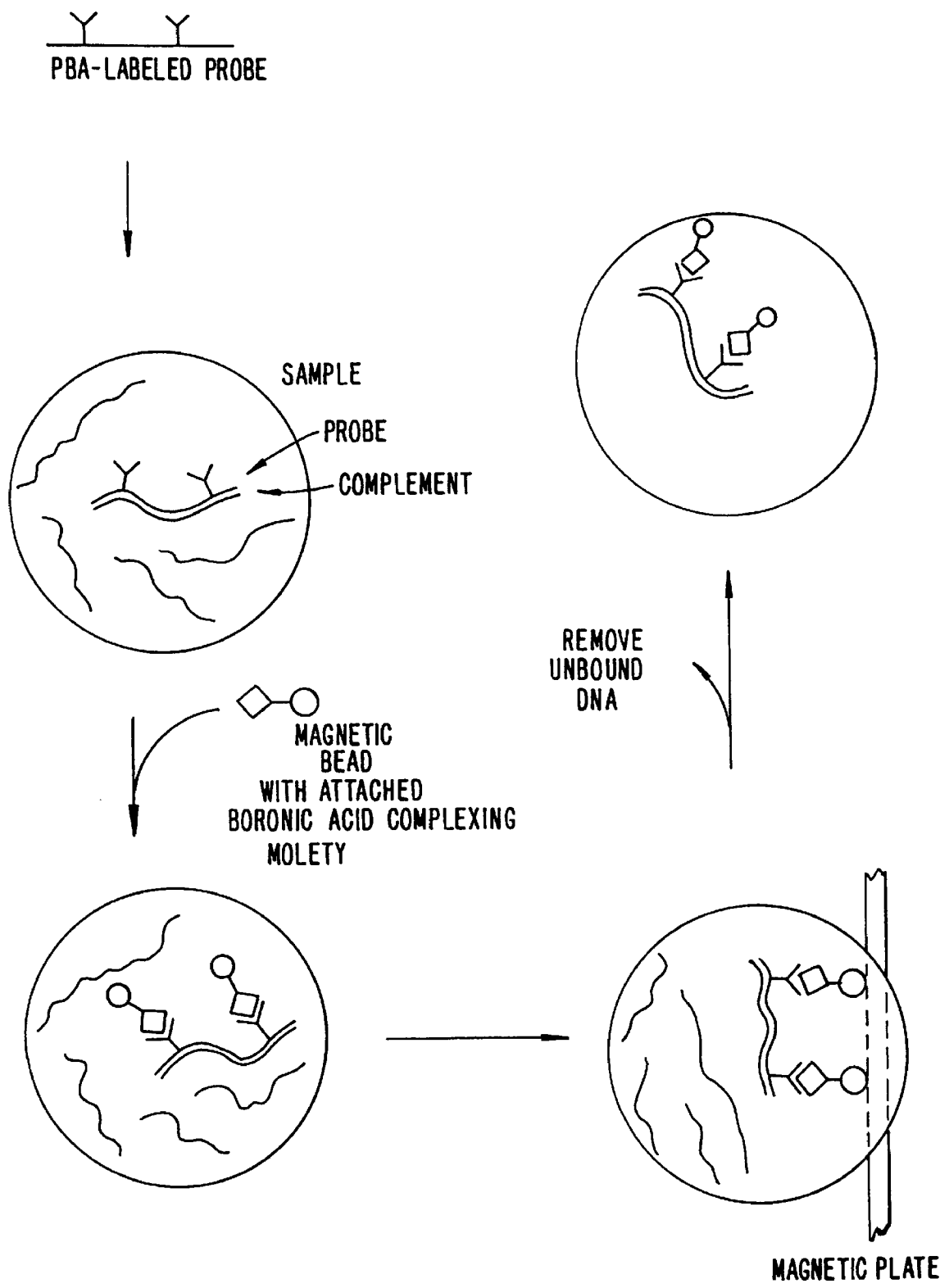
FIG. 5 illustrates the use of modified polynucleotides in affinity purification.

Alternatively, the modified polynucleotides of the present invention can be used for affinity purification of a target polynucleotide, which is illustrated in FIG. 5. In this aspect of the invention, the probes are prepared as described and added to a mixture of polynucleotides containing a target polynucleotide. Following hybridization, magentic beads having an attached boronic acid complexing moiety are placed in the mixture and binding to the PBA-labeled probe occurs. The beads (with attached probe and target) are drawn to a magnetic plate and the remaining materials are washed away.

Still further, the modified polynucleotides can be used in combination with other purification and labeling methods to provide unique methods of isolating and detecting picogram quantities of target polynucleotides (see Examples below).

Accordingly, the present invention provides methods for detecting the presence of a target nucleic acid in a sample, comprising;

(a) contacting a sample with a modified polynucleotide which is substantially complementary to the target nucleic acid under conditions sufficient to hybridize the modified polynucleotide to the target nucleic acid thereby forming a hybridized complex;

(b) contacting the hybridized complex with a complexing agent which comprises a detectable moiety or an indicator and a boronic acid complexing moiety; and (c) detecting the presence of the detectable moiety or indicator, thereby detecting the presence of the target nucleic acid.

The modified polynucleotides used in this aspect of the invention are represented by the formula:

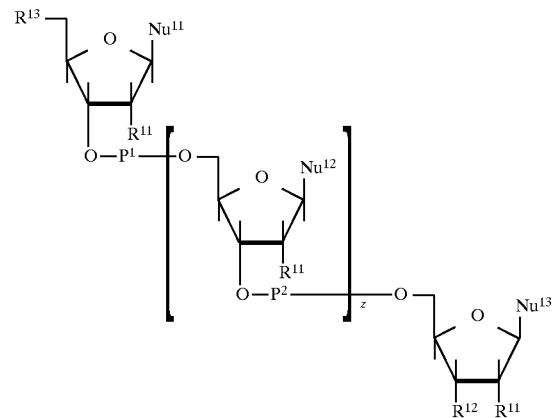

In this formula, z represents an integer of from 1 to 1000 and each $R^{11}$ is —H or —OH. The symbols $R^{12}$ and $R^{13}$ each independently represent a hydroxyl, protected hydroxyl, monophosphate ester, diphosphate ester, or triphosphate ester. The symbols $P^1$ and $P^2$ are each independently —P(O)(OH)—, —P(O)(NH$_2$)—, —P(S)(OH)—, —P(O)(CH$_3$)—, or a pharmaceutically acceptable salt thereof.

In the above formula, each $Nu^{11}$, $Nu^{12}$ and $Nu^{13}$ is independently adenine, guanine, thymine, cytosine or a modified nucleic acid base having the formula:

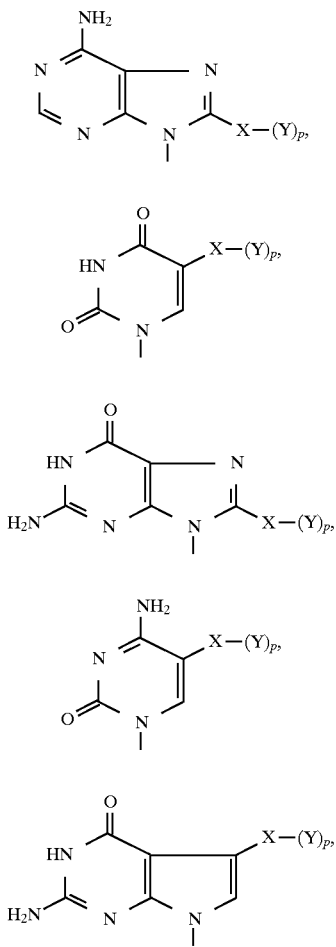

The nucleic acid derivatives above, are modified to have a boron-containing moiety which is attached to the heterocyclic ring portion by means of a linking group X. Typically, the linking group comprises of from 3 to 30 carbon atoms. Preferred groups for X are those which have been described above for the monomers of the present invention. The boron-containing moiety, Y, is a boronic acid substituent such as —B(OH)$_2$, —B(OH)(OR) and —B(OR)(OR') in which R and R' are alkyl groups of from 1 to 6 carbon atoms which, in some embodiments, can be linked together to form a cyclic ester. The letter p represents an integer of from 1 to 3. Preferred groups for Y are also those which have been described above for the monomers.

The modified polynucleosides and polynucleotides of the present invention are constructed such that at least one and no more than thirty of $Nu^{11}$, $Nu^{12}$ and $Nu^{13}$ are other than adenine, guanine, thymine or cytosine. One of skill in the art will understand that the number of modified nucleic acid monomers in a polynucleotide will depend in part on the particular application (e.g., the sensitivity of the complexing agent which is ultimately attached to the boronic acid moiety in various assays). Additionally, the modified monomers should not be so numerous as to interfere with the duplex formation which takes place between the modified polynucleotide and the target polynucleotide (e.g., a target gene or target oligonucleotide). Thus, for example, an oligomer of 20 to 30 monomers will typically contain from one to five modified monomers, while a polymer of 1000 monomers can contain up to about 30 modified monomers.

The sequence of the modified polynucleotide is one which is essentially complementary to the target polynucleotide. As used herein, the term "complementary or substantially complementary" refers to the hybridization or base pairing between nucleotides or nucleic acids, such as, for instance, between the two strands of a double stranded DNA molecule or between an polynucleotide primer and a primer binding site on a single stranded nucleic acid to be sequenced or amplified. Complementary nucleotides are, generally, A and T (or A and U), or C and G. Two single stranded RNA or DNA molecules are said to be substantially complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%.

Alternatively, substantial complementarity exists when an RNA or DNA strand will hybridize under selective hybridization conditions to its complement. Typically, selective hybridization will occur when there is at least about 65% complementarity over a stretch of at least 14 to 25 nucleotides, preferably at least about 75%, more preferably at least about 90% complementarity. See, M. Kanehisa, *Nucleic Acids Res.* 12:203 (1984), incorporated herein by reference.

Stringent hybridization conditions will typically include salt concentrations of less than about 1M, more usually less than about 500 mM and preferably less than about 200 mM. Hybridization temperatures can be as low as 5° C., but are typically greater than 22° C., more typically greater than about 30° C., and preferably in excess of about 37° C. Longer fragments may require higher hybridization temperatures for specific hybridization. As other factors may affect the stringency of hybridization, including base composition and length of the complementary strands, presence of organic solvents and extent of base mismatching, the combination of parameters is more important than the absolute measure of any one alone.

Once a hybridized complex has formed between the boron-containing polynucleotide of the present invention and the target nucleic acid, the complex will be treated with a complexing agent which comprises a detectable moiety (label) or an indicator and a boronic acid complexing moiety.

A variety of boronic acid complexing moieties are useful in this aspect of the present invention. In order for complexing to occur, the complexing moiety should have functionality which can react with a boronic acid group to form a boronic acid ester, or diester. Alternatively, the boronic acid complex which is formed from the modified polynucleotide and the complexing agent can comprise a boron-containing tervalent structure in which one of the boron ligands is the nitrogen of an amine group, an amide group or a hydroxamic acid ester group (see FIG. 1). Accordingly, preferred functionality for the boronic acid complexing agent includes 1,2-diols, 1,3-diols, 1,2-aminoalcohols, 1,3-aminoalcohols, ortho-hydroxybenzohydroxamic acids, ortho-hydroxybenzoic acids, and ortho-hydroxybenzamides. A number of boronic acid complexing moieties have been described in copending applications U.S. Ser. Nos. 08/188, 460, 08/188,531, 08/188,958 and 08/188,176, each of which was filed on Jan. 28, 1994 and is incorporated herein by reference. Additional examples of boronic acid complexing moieties are described in copending applications U.S. Ser. Nos. 08/689,341; 08/691,929; 08/691,930; 08/689,283, which were filed Aug. 5, 1996 as continuations-in-part of one or more of the above applications.

The complexing agents will further comprise a detectable moiety (label) or an indicator. The terms "detectable moiety" or "label" refer to a composition detectable by spectroscopic, photochemical, biochemical, immunochemical, or chemical means. For example, labels useful with a boronic acid complexing agent in hybridization assays include $^{32}P$, $^{35}S$, fluorescent dyes, electron-dense reagents, enzymes (e.g., as commonly used in an ELISA), biotin, dioxigenin, or haptens and proteins for which antisera or monoclonal antibodies are available.

A wide variety of labels suitable for use with nucleic acid hybridization and conjugation techniques described herein are known and are reported extensively in both the scientific and patent literature. Each of the groups of labels are generally applicable to the present invention for incorporation into a boronic acid complexing agent and subsequent labeling of target nucleic acids. Suitable labels include radionucleotides, enzymes, substrates, cofactors, inhibitors, fluorescent moieties, chemiluminescent moieties, magnetic particles, and the like. Labeling agents optionally include e.g., monoclonal antibodies, polyclonal antibodies, proteins, or other polymers such as affinity matrices, carbohydrates or lipids. Detection of the resultant duplex nucleic acids proceeds by any known method, including immunoblotting, tracking of radioactive or bioluminescent markers, Southern blotting, northern blotting, southwestern blotting, northwestern blotting, or other methods which track a molecule based upon size, charge or affinity. The particular label or detectable group used and the particular assay are not critical aspects of the invention. The detectable moiety can be any material having a detectable physical or chemical property. Such detectable labels have been well-developed in the field of gels, columns, solid substrates and in general, labels useful in such methods can be applied to the present invention. Thus, a label is any composition detectable by spectroscopic, photochemical, biochemical, immunochemical, electrical, optical or chemical means. Useful labels in the present invention include fluorescent dyes (e.g., fluorescein isothiocyanate, Texas Red, rhodamine, and the like), radiolabels (e.g., $^{3}H$, $^{125}I$, $^{35}S$, $^{14}C$, or $^{32}P$), enzymes (e.g., LacZ, CAT, horse radish peroxidase, alkaline phosphatase and others, commonly used as detectable enzymes, either as marker gene products or in an ELISA), nucleic acid intercalators (e.g., ethidium bromide) and colorimetric labels such as colloidal gold or colored glass or plastic (e.g. polystyrene, polypropylene, latex, etc.) beads.

The label is coupled directly or indirectly to the boronic acid complexing moiety according to methods well known in the art. As indicated above, a wide variety of labels are used, with the choice of label depending on the sensitivity required, ease of conjugation of the compound, stability requirements, available instrumentation, and disposal provisions. Non radioactive labels are often attached by indirect means. Generally, a ligand molecule (e.g., biotin) is covalently bound to a polymer. The ligand then binds to an anti-ligand (e.g., streptavidin) molecule which is either inherently detectable or covalently bound to a signal system, such as a detectable enzyme, a fluorescent compound, or a chemiluminescent compound. A number of ligands and anti-ligands can be used. Where a ligand has a natural anti-ligand, for example, biotin, thyroxine, and cortisol, it can be used in conjunction with labeled, anti-ligands. Alternatively, any haptenic or antigenic compound can be used in combination with an antibody. Labels can also be conjugated directly to signal generating compounds, e.g., by conjugation with an enzyme or fluorophore. Enzymes of interest as labels will primarily be hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence, e.g., by microscopy, visual inspection, via photographic film, by the use of electronic detectors such as charge coupled devices (CCDs) or photomultipliers and the like. For detection in VLSIPS™ arrays (see U.S. Pat. No. 5,143,854, incorporated herein by reference) fluorescent labels and detection techniques, particularly microscopy are preferred. Similarly, enzymatic labels may be detected by providing appropriate substrates for the enzyme and detecting the resulting reaction product. Finally, simple colorimetric labels are often detected simply by observing the color associated with the label. Thus, in various dipstick assays, conjugated gold often appears pink, while various conjugated beads appear the color of the bead. In some embodiments, the label will be contained in a liposome or latex carrier which is coupled to the boronic acid complexing moiety.

The labels or indicators and the boronic acid complexing moieties which together form the complexing agents are typically joined together by means of a covalent linkage or linking group. In one group of embodiments, the linking group will be similar to those described above for joining together a boronic acid moiety and the heterocyclic base of a nucleotide monomer. More particularly, the linking groups used in joining the components of a complexing agent will comprise from about 3 to about 30 carbon atoms, optionally interrupted by one or more amide, ester, disulfide, urea, carbamate, hydrazone, ether, thioether, amine or imine groups. A requirement of the linking group is that, when coupled to the detectable moiety or label, it does not interfere with the intended purpose or function of the label. Similarly, coupling of the linking group to the boronic acid complexing moiety should not interfere with the ability of the complexing moiety to react with a modified polynucleotide.

Figure 6:
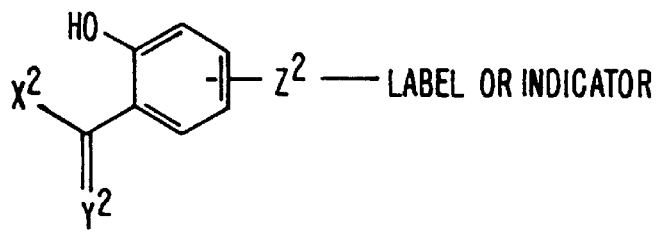
FIG. 6 illustrates complexing agents (labels and boronic acid complexing moieties) and labeled complexes which can be formed.
Figure 6:
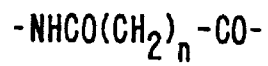
Figure 6:
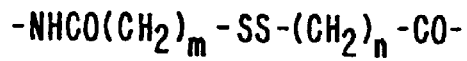
Figure 6:
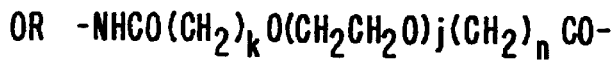
Figure 6:
Figure 6:
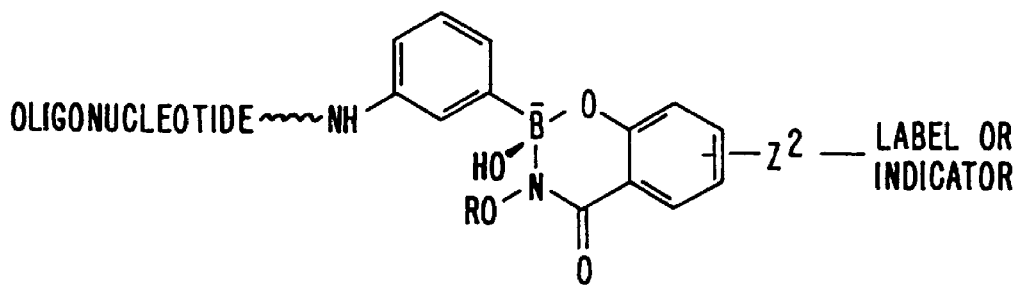

In one group of embodiments, the complexing agent will have the formula:

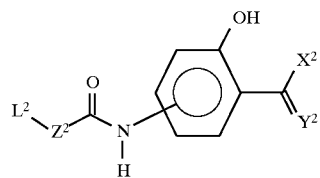

in which $X^2$ is OH, OR, $NH_2$, NHR, NHOH or NHOR, in which R is an alkyl group of from one to six carbon atoms, either branched or straight chain. $Y^2$ is O, S or NH, preferably O. $Z^2$ is a linking group and $L^2$ is the label or indicator. Thus, the hydroxy-substituted aromatic ring together with the functionality comprising $X^2$ and $Y^2$ is the boronic acid complexing moiety. The linking group in these embodiments is typically an alkylene chain having from one to ten carbon atoms, saturated or unsaturated, which is optionally interrupted by one or more disulfide bonds, esters or amides. Examples are provided in FIG. 6. Thus, when the linking group is derived from an alkyl halide, a label having a pendant thiol group may be attached. Alternatively, when the linking group is derived from an ester, the ester can be converted to an acid hydrazide and attached to a label having a pendant aldehyde group (which can be the result of periodate oxidation of a carbohydrate). Still further, when the linking group is derived from a carboxylic acid, it may be further functionalized by reaction with dicyclohexylcarbodiimide (DCC) and an activating group such as, for example, N-hydroxysuccinimide (NHS) or N-hydroxysulfosuccinimde (SNHS). The resulting activated ester can be used to attach a label having a pendant amine moiety.

Figure 7:
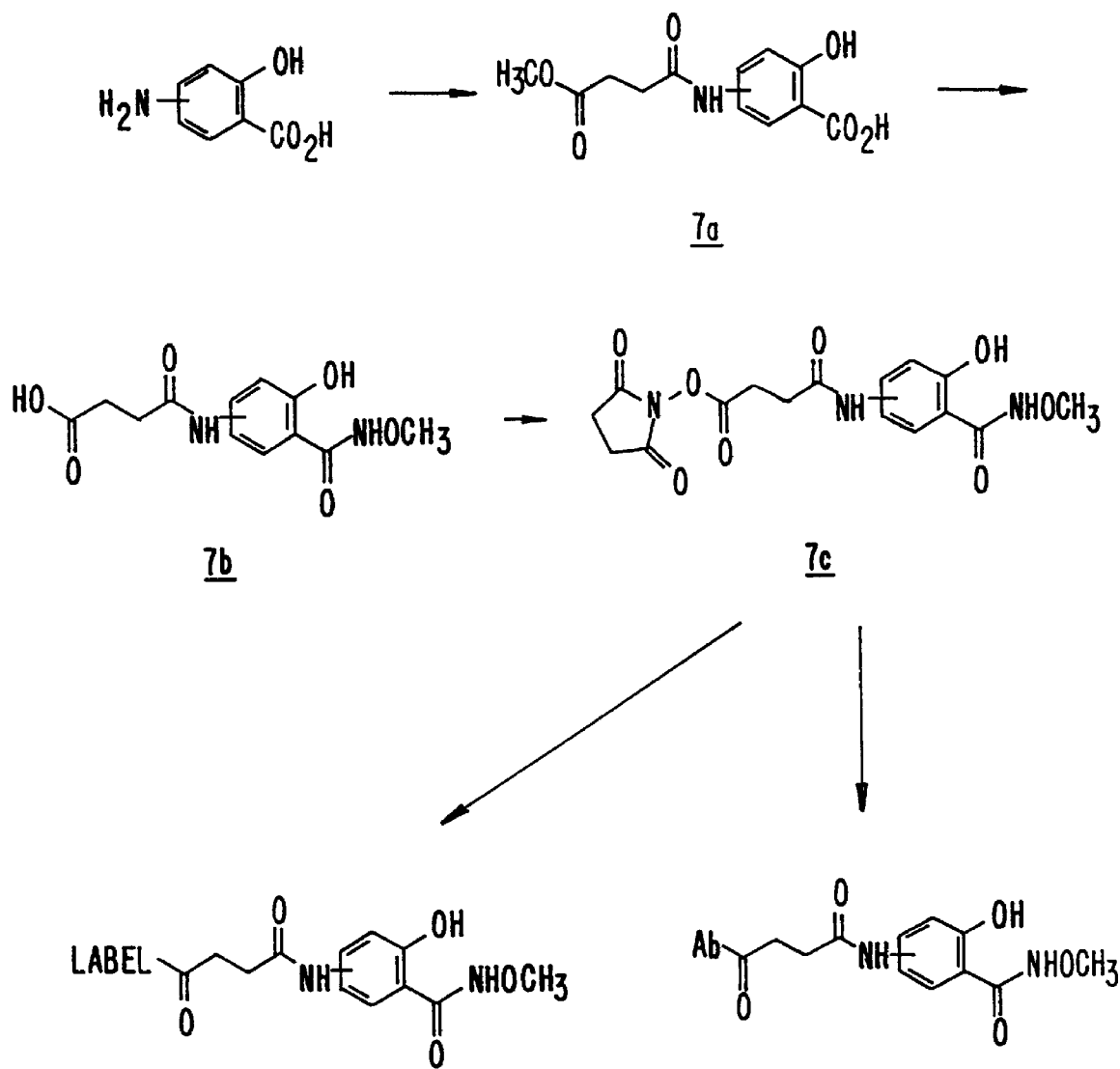
FIGS. 7–17 provide reaction schemes for the preparation of complexing agents and the intermediates to which appropriate labels can be attached.

In particularly preferred embodiments, a complexing agent can be prepared by the methods outlined in FIG. 7. For example, amino salicylic acid can be treated with methyl succinyl chloride to produce the amide 7a in FIG. 7. Conversion of the carboxylic acid functionality to a N-methoxy benzamide followed by saponification of the ester results in 7b. Esterification with the activating group NHS provides a compound 7c. The activated compound 7c can be used to couple a label or an antibody, described in detail hereinbelow.

Figure 8:
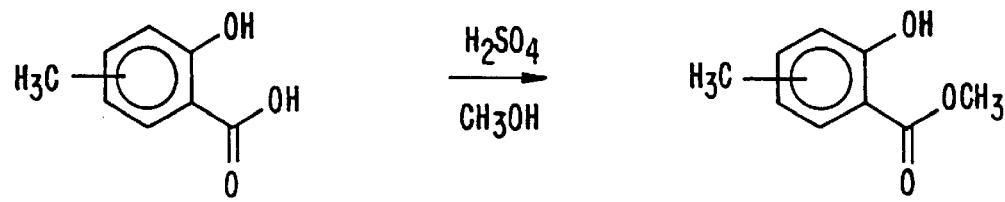
Figure 8:
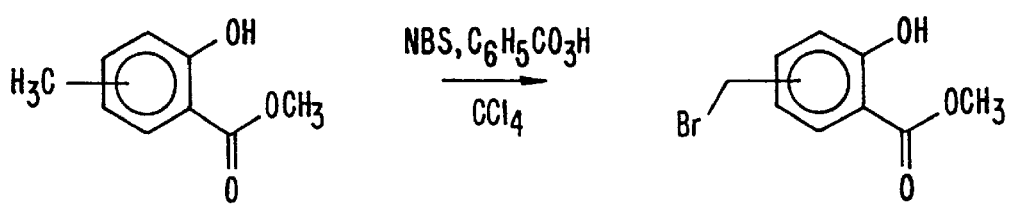
Figure 8:
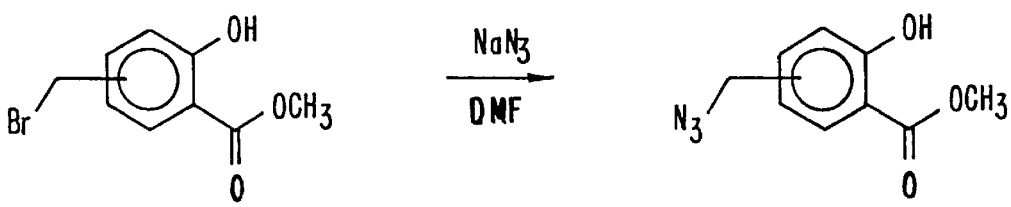
Figure 8:
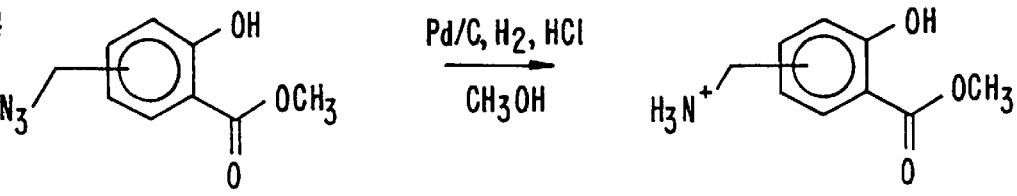
Figure 9:
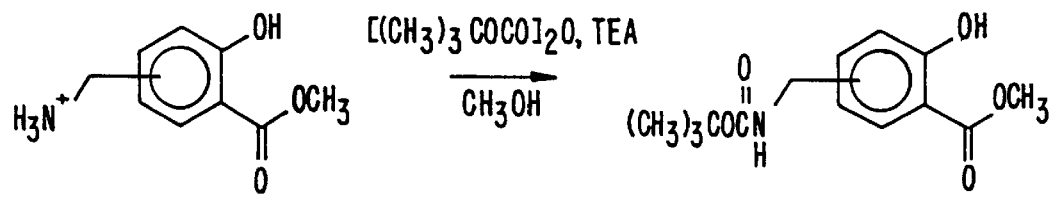
Figure 9:
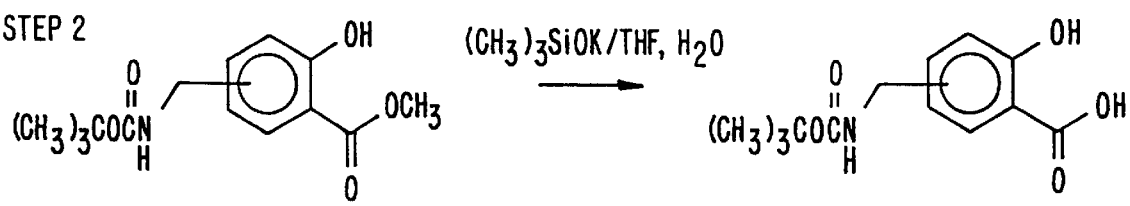
Figure 9:
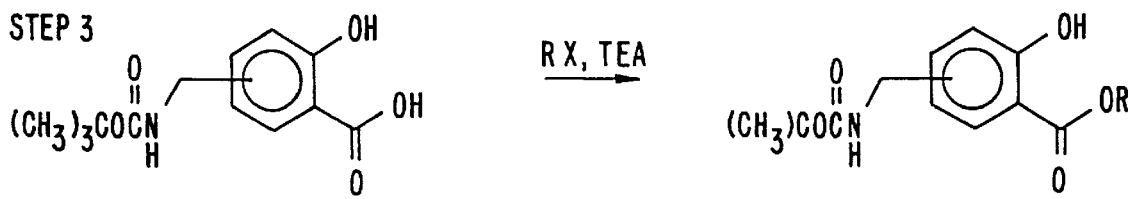
Figure 9:
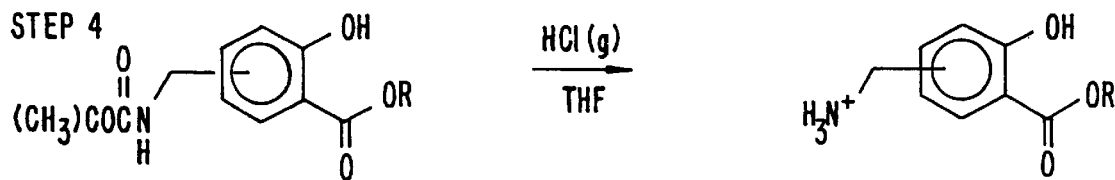
Figure 10:
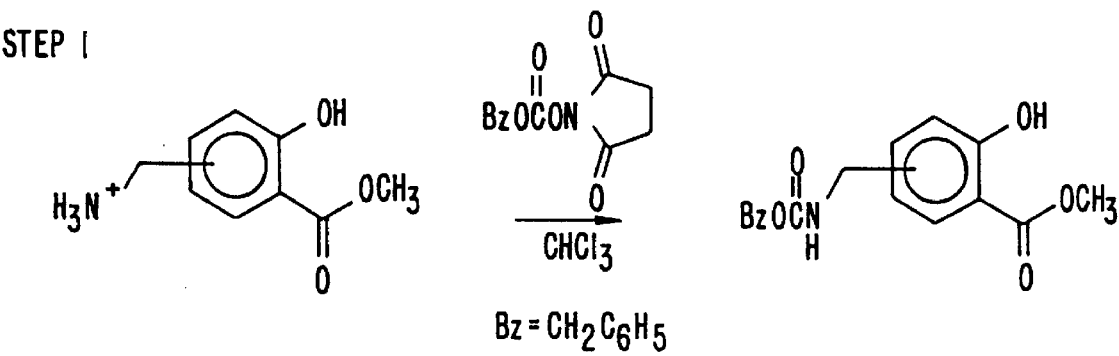
Figure 10:
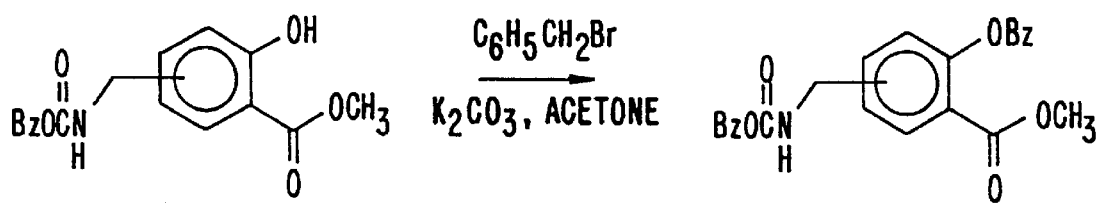
Figure 10:
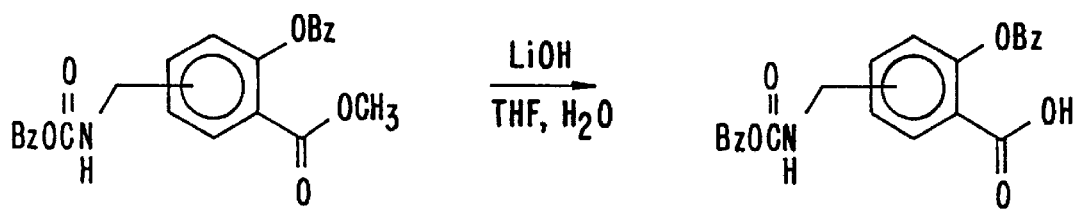
Figure 10:
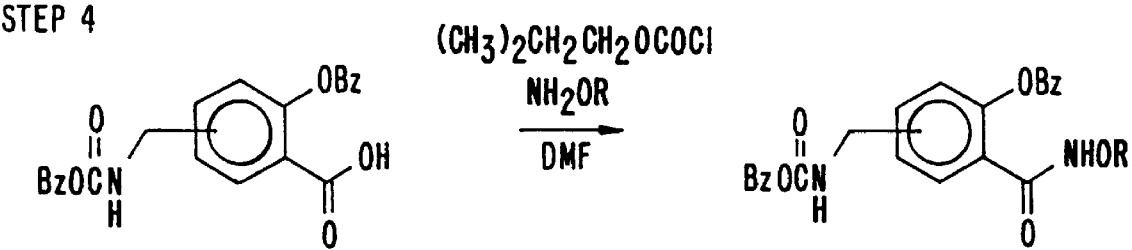
Figure 10:
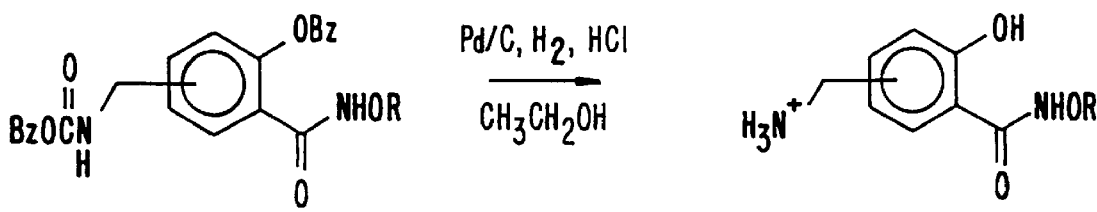
Figure 11:
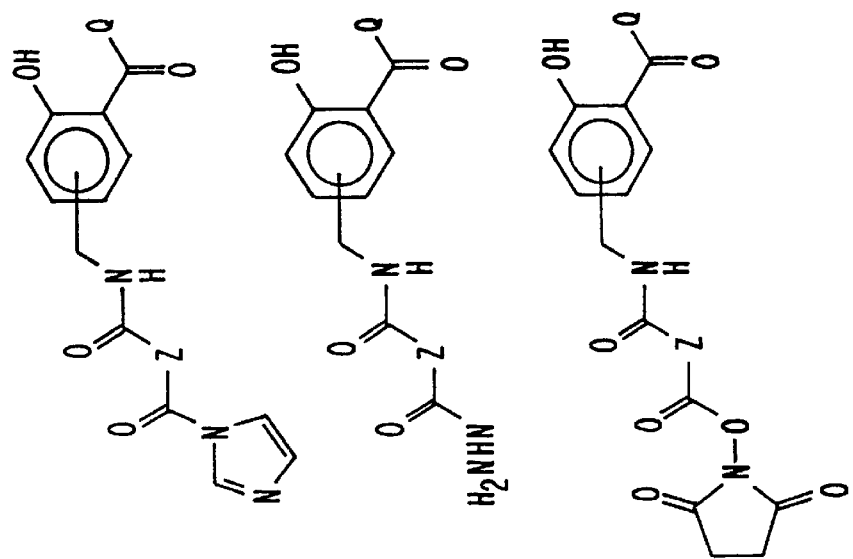
Figure 11:
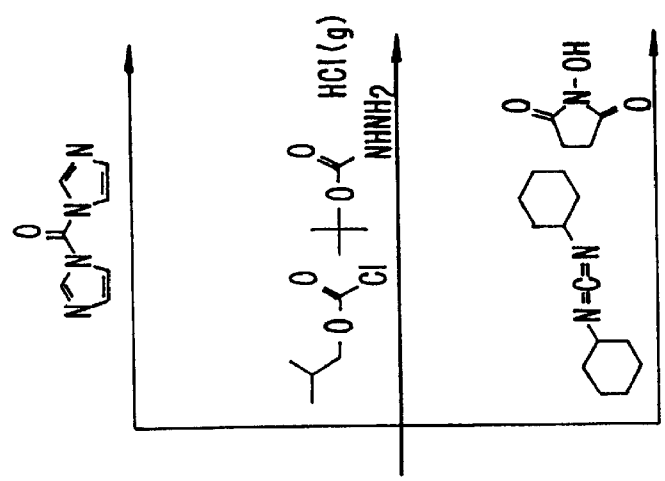
Figure 11:
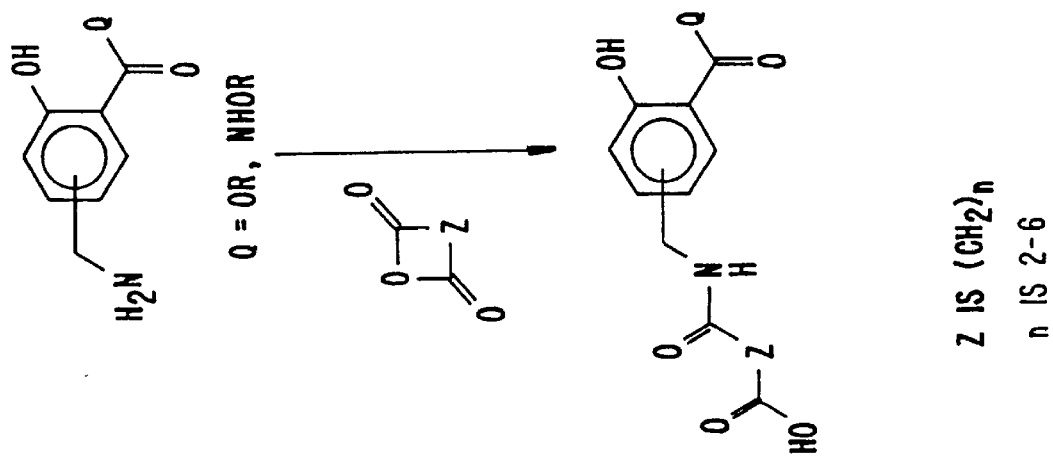
Figure 12:
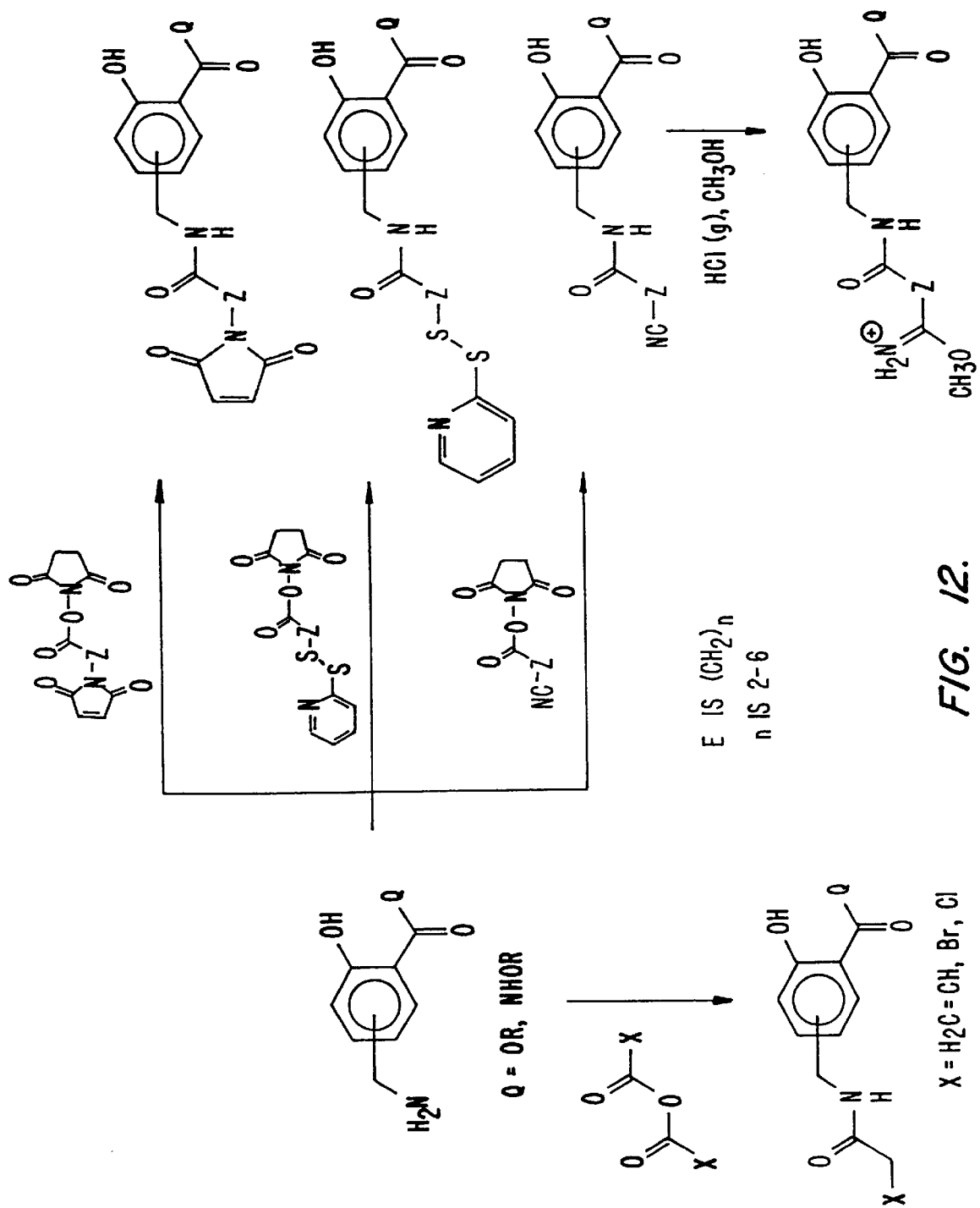
Figure 13:
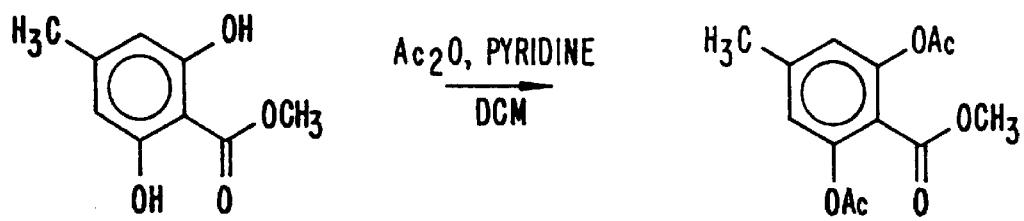
Figure 13:
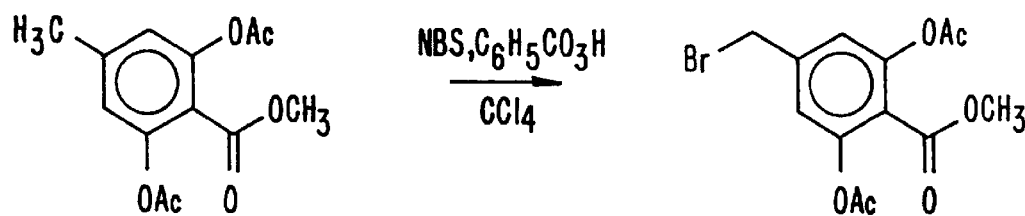
Figure 13:
Figure 13:
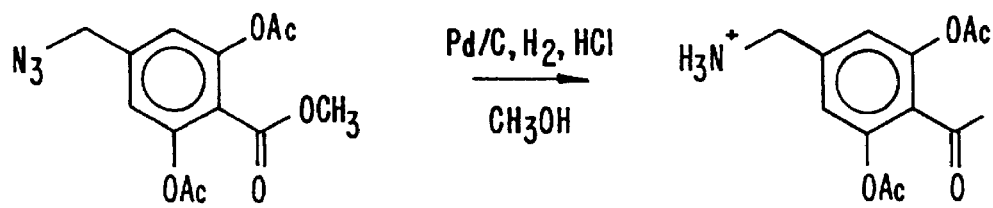
Figure 13:
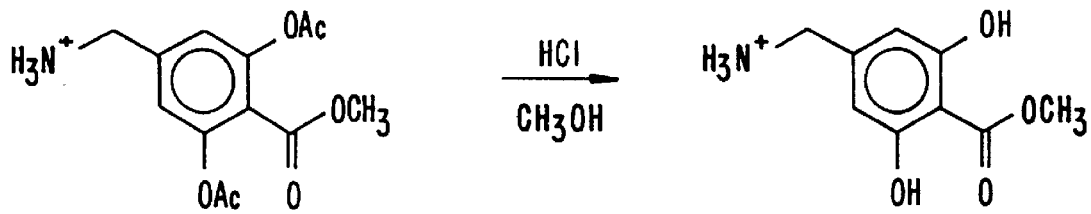
Figure 14:
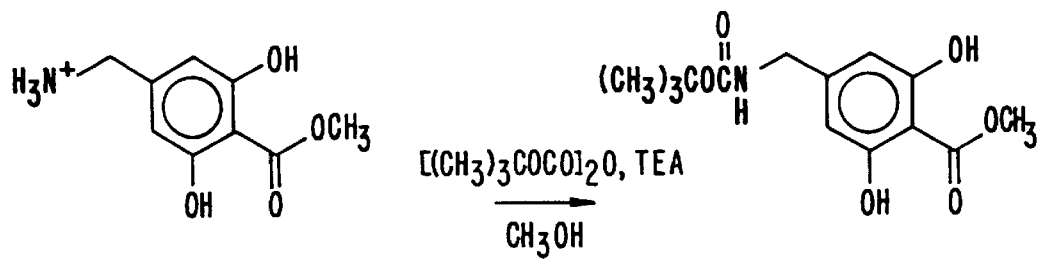
Figure 14:
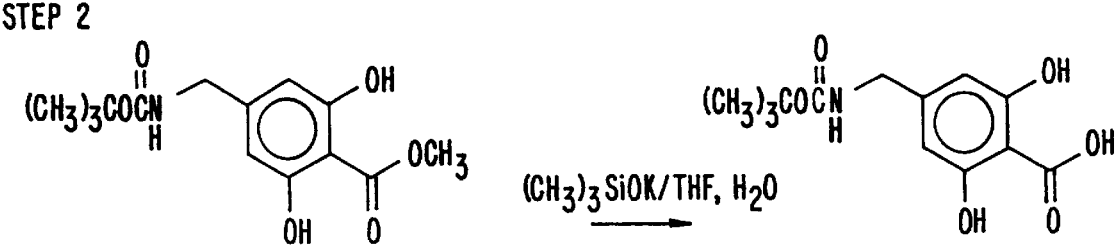
Figure 14:
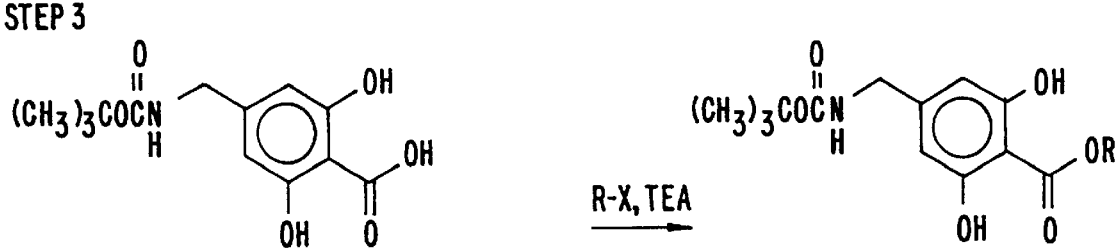
Figure 14:
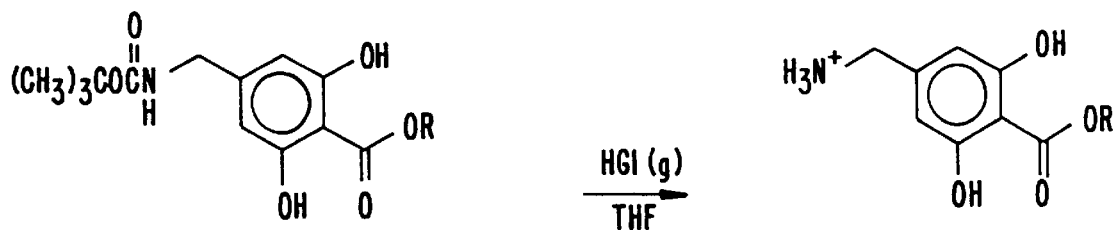
Figure 15:
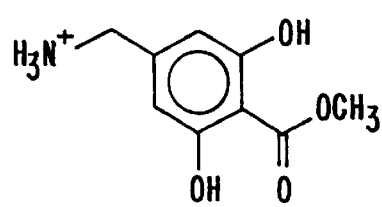
Figure 15:
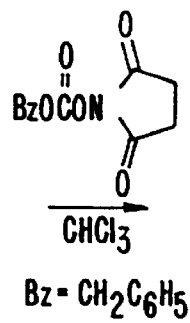
Figure 15:
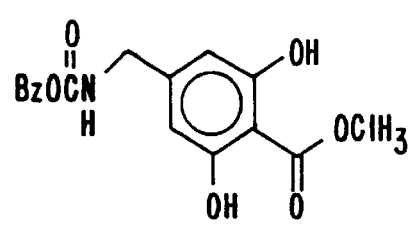
Figure 15:
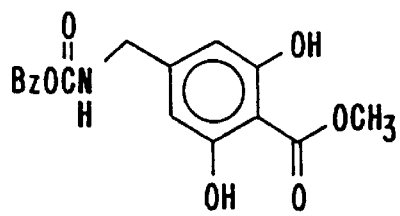
Figure 15:
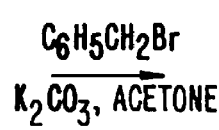
Figure 15:
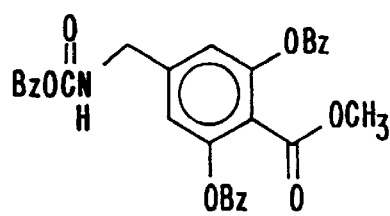
Figure 15:
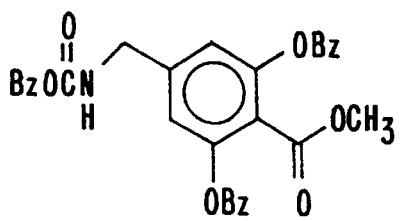
Figure 15:
Figure 15:
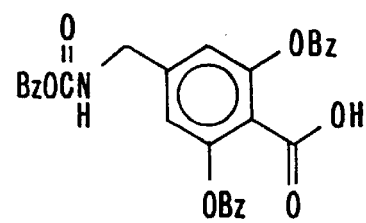
Figure 15:
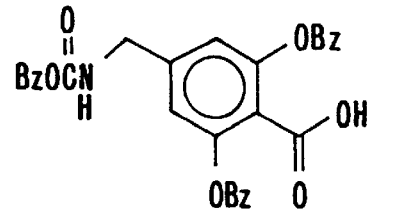
Figure 15:
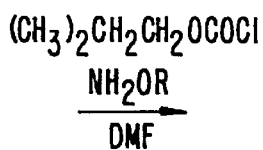
Figure 15:
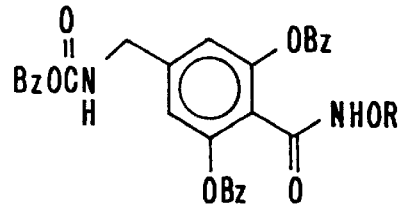
Figure 15:
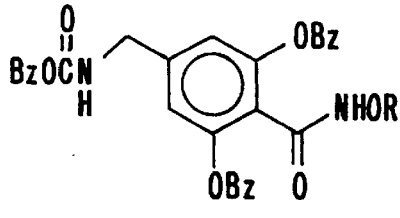
Figure 15:
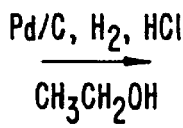
Figure 15:
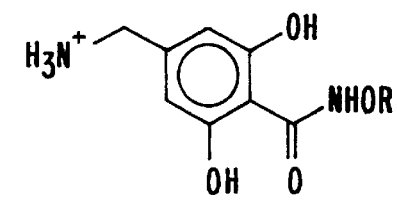
Figure 16:
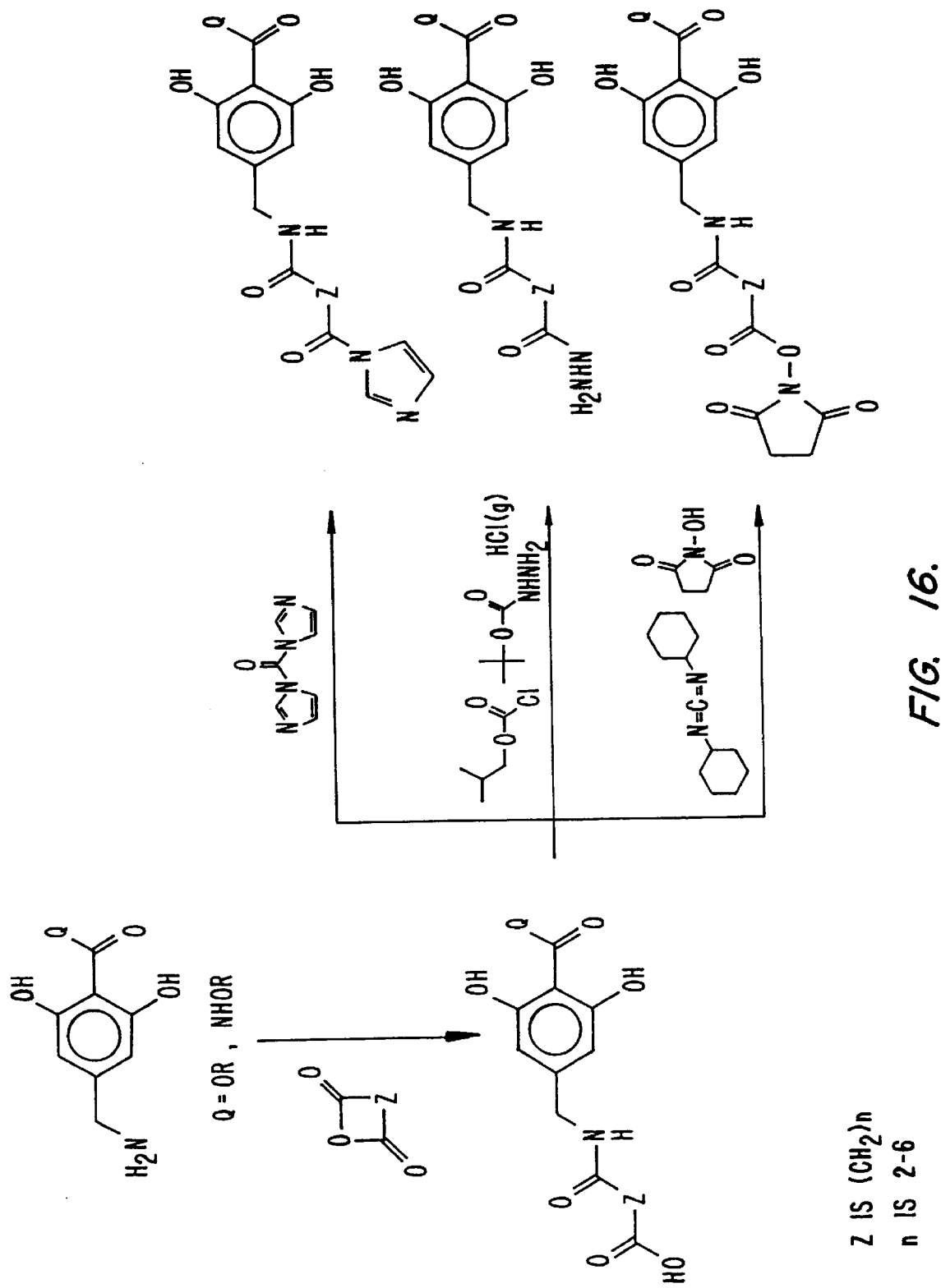
Figure 17:
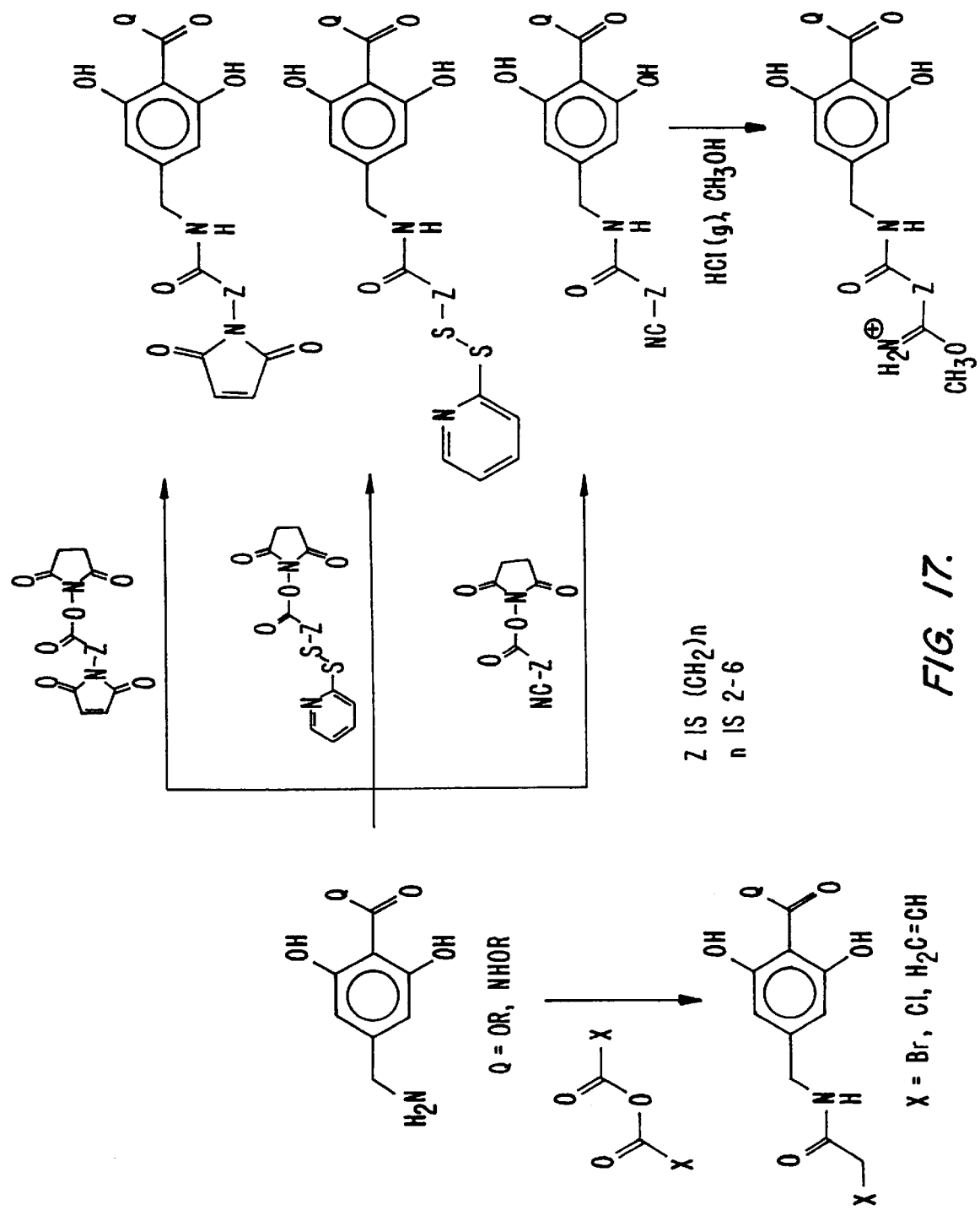

In another group of embodiments, the complexing agent with have the formula:

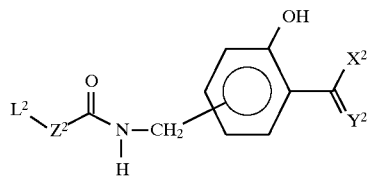

in which $L^2$, $X^2$, $Y^2$, $Z^2$ and R are as described above. Complexing agents of this general formula can be prepared by standard synthetic methods using intermediates prepared as shown in FIGS. 8–12. In FIG. 8, 3-, 4- or 5-methylsalicylic acid is esterified with methanol and acid, then brominated with N-bromosuccinimide. The resulting benzylic bromide is converted to a benzylic azide with sodium azide in DMF. Reduction of the azide to an amine is accomplished using catalytic hydrogenation. In FIG. 9, transesterification of the benzoate ester is carried out by first protecting the amine as its t-butyl carbamate (t-BOC), saponification of the methyl ester, re-esterification with RX (in which X denotes a leaving group such as a halide or tosylate), and cleavage of the protecting group. FIG. 10 shows the conversion of the methyl ester (of FIG. 8) to an alkylhydroxamic acid. In this scheme the amine is protected as its benzyloxycarbamate and the hydroxyl group is protected as its benzyl ether. The methyl ester is then saponified and the resulting acid is converted to its alkylhydroxamic acid. Removeal of both protecting groups is accomplished with catalytic hydrogenolysis. The compounds produced in FIGS. 8–10 are then provided with additional linking groups and reactive functionality for the attachment of suitable labels as outlined in FIGS. 11 and 12. Selection of the appropriate reactive functionality and subsequent coupling of the label will depend on the functionality present on the label to be attached. Criteria for appropriate selection have been described above and are well known to those of skill in the art.

In yet another group of embodiments, the complexing agent will have the formula:

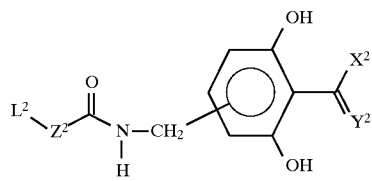

in which $L^2$, $X^2$, $Y^2$, $Z^2$ and R again have the meanings described above. Schemes for the preparation of intermediates are shown in FIGS. 13–17. Coupling of a label to and appropriate intermediate will follow methods described above and known to those of skill in the art.

In some preferred embodiments the label portion of the complexing agent will be a marker enzyme such as, for example, alkaline phosphatase and horseradish peroxidase (HRP). When alkaline phosphatase is used as the label or indicator, detection is typically achieved using a dye substrate, bioluminescence or chemiluminescence following techniques known to those of skill in the art. See, for example, Marich, et al. in NONRADIOACTIVE LABELING AND DETECTION OF BIOMOLECULES (Kessler, ed.) pp. 143–149, Springer-Verlag, Berlin/Heidelberg, and Miska, et al., *J. Biolumin. Chemilumin.* 4:119–128 (1990), the disclosures of each being incorporated herein by reference.

Following contacting a complexing agent with a hybridized complex, any excess complexing agent is typically removed using conventional techniques such as, for example, gel filtration or chromatography. The hybridized complex with the attached complexing agent can then be detected by conventional means as described above and in reviews such as NONISOTOPIC DNA PROBE TECHNIQUES, Academic Press, Chapter 1, Krichta, ed. (1992) and NONISOTOPIC PROBING, BLOTTING, AND SEQUENCING, Academic Press, Chapter 2, Kessler, ed. (1995), each of which has previously been incorporated herein by reference.

In other aspects, the modified polynucleotides can be used for affinity purification of target polynucleotides. For example, a sample containing a target nucleic acid can be treated with a modified polynucleotide according to the present invention, under conditions wherein a duplex is formed. The resulting solution containing the duplex having an attached boronic acid moiety can be purified by placement on a solid support having attached boronic acid complexing agents. Materials which do not bind to the solid support can be removed and the target polynucleotide/duplex can then be stripped from the column by conventional methods (e.g., a boric acid wash).

The following examples are offered solely for the purposes of illustration, and are intended neither to limit nor to define the invention.

EXAMPLE 1

This example illustrates the preparation of PBA-XX-dUTP.

1.1 Synthesis of PBA-X-NHS

3-Aminophenylboronic acid succinamic acid (PBA-X-CO₂H).

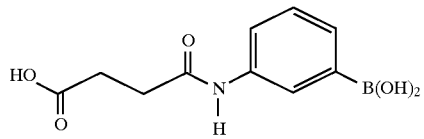

Synthesis of this material was accomplished using a modification of the procedure in Weith, et al. *Biochemistry* 9:4396–4401 (1970). 3-Amino-phenylboronic acid hemisulfate (100 g, 0.535 moles) was suspended in anhydrous pyridine (240 mL). The mixture was stirred magnetically and chilled in an ice/water bath under an atmosphere of dry nitrogen. Succinic anhydride (56.5 g, 0.565 moles) was added to the flask, and the reaction mixture was allowed to warm to room temperature. After stirring overnight (at least 12 hours), all solids had dissolved. The majority of the pyridine was removed on a rotary evaporator (bath temperature ≦55° C.) to give a viscous, amber-colored syrup. The syrup was co-evaporated with water (100 mL), and the residue was then dissolved in water (700 mL). The amber solution was chilled in an ice-water bath, and concentrated hydrochloric acid (30–50 mL) was added slowly to yield a final pH of 1 (pH paper). During this addition, a white solid precipitated. The suspension was chilled for 1 hour at 4° C. The solid was filtered and washed with cold water (100 mL). The solid was then crystallized from hot water, and dried in vacuo over KOH pellets. Yield: 100 g (80%); m.p. 171°–172° C. (open capillary, uncorrected). ¹H NMR (300 MHz, DMSO-d₆): δ 12.07 (broad singlet, 1H, CO₂H), 9.83 (singlet, 1H, ArNHCOR), 7.95 (singlet, 2H, BOH), 7.67 (singlet, 1H, ArH), 7.65 (doublet, J=7.9 Hz, 1H, ArH), 7.41 (doublet, J=7.0 Hz, 1H, ArH), 7.20 (apparent triplet, J=7.8 Hz, 1H, ArH), 2.60–2.40 (multiplet, 4H, COCH₂). ¹³C NMR (75.5 MHz, DMSO-d₆) δ 174.2, 170.2, 138.7, 129.0, 127.8, 125.2, 121.2, 31.0, 28.9. HPLC: Retention time of product, 8.6±0.1 minutes using an Applied Biosystems/Brownlee Aquapore Butyl 2.1×220 mm cartridge, and a mixed gradient elution as follows: A, 0.1M triethylammonium acetate, pH 6.5; B, methanol at a flow rate of 0.5 mL/minute beginning with 100% A/0% B, for 5 minutes, then to 0% A/100% B over 30 minutes at ambient temperature. Detection was carried out using a diode array detector: 260 nm, 280 nm, 300 nm. The sample amount was 5 mg/mL in methanol.

Trimethylene-3-aminophenylboronate succinamic acid succinimidyl ester (PBA-X-NHS)

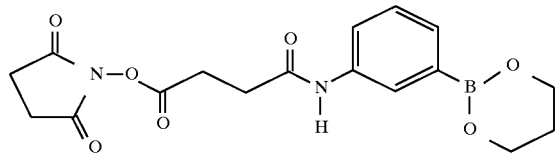

Synthesis of this material was accomplished using a modification of the procedure in Ho, et al. *Biochemistry* 20:64–67 (1981). PBA-X-CO₂H (28.4 g, 0.120 moles) was suspended in dry dioxane (120 mL), and 1,3-propanediol (9.1 g, 0.120 moles) was added. The mixture was gently heated until all solid dissolves (about 10 minutes). The solvent was removed by rotary evaporation to leave a pale yellow syrup, which was co-evaporated twice with dioxane (50 mL each). The residue was then dissolved in dioxane (450 mL) and N-hydroxysuccinimide (14.9 g, 0.130 moles) was added, followed by N,N-dicyclohexylcarbodiimide (26.3 g, 0.128 moles). The solution was stirred under an atmosphere of dry nitrogen for 4 hours at room temperature, during which time the white precipitate of N,N-dicyclohexylurea formed. The precipitate was filtered and washed with dioxane (50 mL). The combined filtrates were concentrated to about 100 mL. Dry diethyl ether (400 mL) was slowly added to the stirred concentrate, causing precipitation of a while solid. The mixture was chilled in an ice/water bath for 1 hour, then filtered. The solid was washed with dry ether (100 mL), and dried in vacuo. Yield: 42.5 g (95%); m.p. 163°–170° C. (open capillary, uncorrected). ¹H NMR (300 MHz, DMSO-d₆): δ 9.99 (singlet, 1H, ArNHCOR), 7.87 (singlet, 1H, ArH), 7.65 (doublet, J=8.0 Hz, 1H, ArH), 7.32 (doublet, J=7.3 Hz, 1H, ArH), 7.22 (triplet, J=7.6 Hz, 1H, ArH), 4.09 (triplet, J=5.4 Hz, 4H, BOCH₂CH₂), 2.95 (triplet, J=6.7 Hz, 2H, succinyl COCH₂), 2.79 (singlet, 4H, succinimidyl COCH₂), 2.69 (triplet, J=6.7 Hz, 2H, succinyl COCH₂), 1.98 (quintet, J=5.4 Hz, 2H, BOCH₂CH₂). ¹³C NMR (75.5 MHz, DMSO-d₆): δ 174.4, 169.0, 168.9, 138.7, 128.4, 128.1, 124.3, 121.4, 61.6, 30.3, 26.9, 25.7, 25.4.

1.2 Synthesis of PBA-XX-NHS

3-Aminophenylboronic acid succinamidohexanoic acid (PBA-XX-CO₂H)

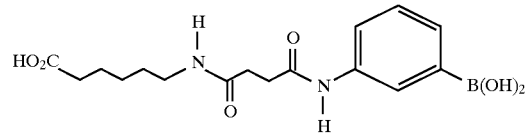

6-Aminohexanoic acid (5.8 g, 0.044 moles) was suspended in dry dioxane (300 mL), and N,N-diisopropylethylamine (15 mL) was added. The suspension was briskly stirred while being chilled in an ice/water bath. PBA-X-NHS (15.0 g, 0.040 moles) was added, and the mixture was stirred under dry nitrogen for 5 minutes. Methanol (300 mL) was then added, the ice bath was removed, and the reaction was allowed to warm to room temperature. After 1 hour, most of the solid has dissolved, and the reaction mixture was evaporated to dryness to leave a pale yellow syrup. This syrup was co-evaporated twice with water (40 mL each) and then dissolved in water (120 mL). The aqueous solution was chilled in an ice/water bath, and the solution was titrated to about pH 1 with concentrated hydrochloric acid (about 1 mL). A white precipitate formed during this time. The suspension was chilled for an additional hour and then filtered. The solid was washed with cold water (10 mL) and then dried in vacuo over KOH pellets. Yield: 10.0 g (70%); m.p. 174°–177° C. (open capillary, uncorrected). ¹H NMR (300 MHz, DMSO-d₆): δ 11.98 (singlet, 1H, CO₂H), 9.84 (singlet, 1H, ArNHCOR), 7.97 (singlet, 2H, BOH), 7.83 (triplet, J=5.4 Hz, 1H, CONHCH₂), 7.81 (singlet, 1H, ArH), 7.68 (doublet, J=8.2 Hz, 1H, ArH), 7.44 (doublet, J=7.3 Hz, 1H, ArH), 7.22 (doublet of doublets, J=7.8 Hz, 1H, ArH), 3.00 (apparent quartet, J=6.3

Hz, 2H, CONHCH₂), 2.52 (triplet, J=7.1 Hz, 2H, COCH₂), 2.36 (triplet, J=7.1 Hz, 2H COCH₂), 2.17 (triplet, J=7.3 Hz, 2H CH₂CH₂CO₂H), 1.50–1.41 (multiplet, 2H, NHCH₂CH₂), 1.39–1.32 (multiplet, 2H, CH₂CH₂CO₂H), 1.28–1.23 (multiplet, 2H, CH₂CH₂CH₂). ¹³C NMR (75.5 MHz, DMSO-d₆): δ 174.7, 171.3, 170.6, 138.7, 128.9, 127.8, 125.2, 121.2, 38.4, 33.6, 31.7, 30.4, 28.9, 26.0, 24,2. HPLC: Retention time of product, 14.3±0.1 minutes using an Applied Biosystems/Brownlee Aquapore Butyl 2.1×220 mm cartridge, and gradient elution as follows: Eluant A, 0.1M triethylammonium acetate, pH 6.5, and B, methanol, at a flow rate of 0.5 mL/minute with 100% A/0% B, 5 minutes, then to 0% A/100% B over 30 minutes at ambient temperature. Detection of the product was carried out using a diode array detector: 260 nm, 280 nm, 300 nm.

Trimethylene-3-aminophenylboronate succinamidohexanoic acid succinimidyl ester (PBA-XX-NHS)

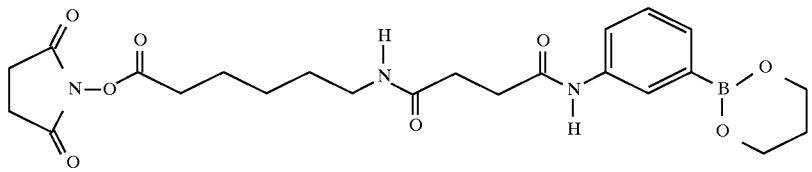

PBA-XX-CO₂H (6.3 g, 0.018 moles) was suspended in dry dioxane (60 mL). 1,3-Propanediol (1.4 g, 0.018 moles) was added, and the mixture was gently heated until all solid dissolves (about 10 minutes). The solvent was removed by rotary evaporation to leave a pale yellow syrup, which was co-evaporated twice with dioxane (30 mL each). The residue was then dissolved in dioxane (225 mL) and N-hydroxysuccinimide (2.3 g, 0.20 moles) was added, followed by N,N-dicyclohexylcarbodiimide (4.1 g, 0.020 moles). The solution was stirred under an atmosphere of dry nitrogen for 6 hours at room temperature, during which time the white precipitate of N,N-dicyclohexylurea formed. The precipitate was filtered and washed with dioxane (50 mL). The combined filtrates were concentrated to about 30 mL. Dry diethyl ether (200 mL) was slowly added to the stirred concentrate, causing precipitation of a white solid. The mixture was chilled in an ice/water bath for 1 hour, then filtered. The solid was washed with dry ether (50 mL), and dried in vacuo. Yield: 8.0 g (91%); M.P. 111°–117° C. (open capillary, uncorrected). ¹H NMR (300 MHz, DMSO-d₆) δ 9.85 (singlet, 1H, ArNHCOR), 7.85 (singlet, 1H, ArH), 7.82 (triplet, J=5.7 Hz, 1H, ArNHCOR), 7.64 (doublet, J=7.9 Hz, 1H, ArH), 7.29 (doublet, J=7.3 Hz, 1H, ArH), 7.22 (doublet of doublets, J=7.6 Hz, 1H, ArH), 4.07 (triplet, J=5.4 Hz, 4H, BOCH₂CH₂), 3.05–2.95 (multiplet, 2H, CONHCH₂), 2.79 (singlet, 4H succinimidyl COCH₂), 2.62 (triplet, J=7.3 Hz, 2H, CH₂CO₂.R), 2.50 (triplet, J=6.7 Hz, 2H, NHCOCH₂), 2.36 (triplet, J=6.7 Hz, 2H, NHCOCH₂, 1.50–1.41 (multiplet, 2H, NHCH₂CH₂), 1.97 (quintet, J=5.4 Hz, 2H, BOCH₂CH₂), 1.61–1.51 (multiplet, 2H, CH₂), 1.41–1.30 (multiplet, 4H, CH₂). ¹³C NMR (75.5 MHz, DMSO-d₆) δ 171.3, 170.6, 170.5, 169.2, 138.9, 128.1, 128.0, 124.3, 121.4, 61.5, 38.2, 31.7, 30.4, 30.1, 28.6, 26.8, 25.4, 23.9, 15.1. HPLC: Retention time of product, 18.2±0.1 minutes under the conditions described above.

1.3 Synthesis of 5-aminoallyl-dUTP

Synthesis of this material was accomplished using a modification of the procedure in Langer, et al., *Proc. Natl. Acad. Sci. USA*, 78:6633–6637 (1981).

5-Chlormercurideoxyuridine 5'-triphosphate (5-ClHg-dUTP)

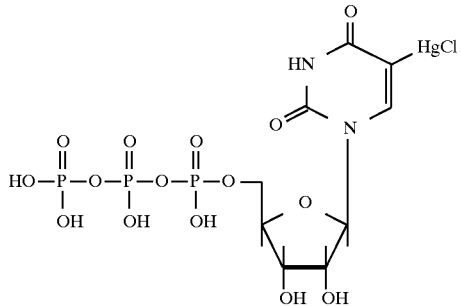

Deoxyuridine 5'-triphosphate (600 mg, about 1 mmole) was dissolved in 0.1M aqueous sodium acetate. pH 6.0 (100 mL). The solution was warmed in an oil bath (bath temperature 50°–55° C.), and mercuric chloride (1.6 g, 5 mmoles) was added. The solution was stirred at 50°–55° C. for 4 hours, then cooled to room temperature. Lithium chloride (424 mg, 10 mmoles) was added, and the solution was stirred for 30 minutes. During this time, the solution turned cloudy. The aqueous mixture was then extracted five times with ethyl acetate (100 mL each). Following the extractions, the aqueous solution was chilled in an ice/water bath, stirred briskly, and ice-cold ethanol (400 mL) was added. A fluffy white precipitate forms. The solid was collected at –20° C. overnight, then filtered, washed with cold ethanol (150 mL) and then diethyl ether (100 mL), and dried in vacuo at 60° C. Yield: 772 mg. λ$_{max}$: 267 nm [ε=10,000M⁻¹ cm⁻¹] (0.1M sodium acetate, pH 5.0)

5-Aminoallyldeoxyuridine 5'-triphosphate (5-AA-dUTP)

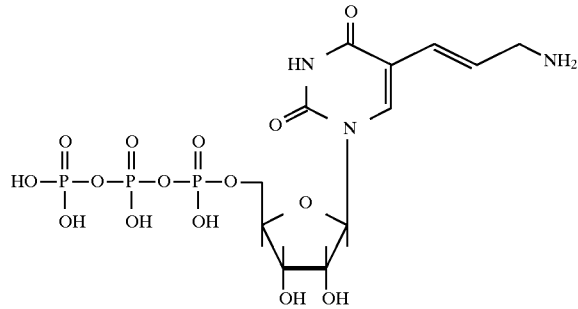

5-ClHg-dUTP (160 mg) was dissolved in 0.1M aqueous sodium acetate, pH 5.0 (10 mL), to give a slightly cloudy solution. An aliquot (5 mL) of this solution was diluted with 0.1M sodium acetate, pH 5.0 (1.0 mL), and the ultraviolet spectrum was measured. The concentration of the stock 5-ClHg-dUTP solution was then calculated from the extinction coefficient and the dilution factor to be 20 mM, or 200

μmoles 5-ClHgdUTP in the 10 mL of solution. An aliquot (1.2 mL, 2.4 mmoles) of a fresh, ice-cold solution of allylamine (1.5 mL) in 4M aqueous acetic acid (8.5 mL) was then added to the stirred 5-ClHg-dUTP solution, followed by a solution of potassium tetrachloropalladate (65 mg, 200 μmoles) in water (1.6 mL). The reaction mixture darkens rapidly, and a black precipitate forms. The reaction was allowed to proceed for 4 hours at room temperature, then overnight at 4° C. The mixture was filtered through a 0.45 mm nylon membrane. The product was isolated from the pale yellow filtrate by ion exchange HPLC, using an Alltech HEMA-IEC BIO 1000 DEAE column, 250×7.5 mm, and a gradient of 0.0M to 0.5M lithium chloride in 25 mM MES buffer, pH 6.1, over 20 minutes. The flow rate was 2.0 mL/minute. Absorbance was monitored at 320 nm. A 1.0 mL aliquot of the filtrate was injected for each run. The peak at about 13 minutes contained the desired product and was collected. The product fractions were combined and concentrated to about 5 mL. Ice-cold ethanol (20 mL) was added to the product solution, and a white precipitate formed. The mixture was chilled at −20° C. overnight. The precipitate was pelleted by centrifugation (3000 rpm, 20 minutes, 4° C.). The supernatant was decanted and the pellet was dissolved in 0.5 mL of deionized water. The concentration of the product solution was calculated from the absorbance at 290 nm ($\epsilon \equiv 7100 M^{-1}\ cm^{-1}$). The yield was about 30%. This stock solution was stored frozen. $\lambda_{max}$: 240, 290 nm; $\lambda_{min}$: 264 nm (water).

1.4 Synthesis of PBA-XX-dUTP 5-(3-aminophenylboronic acid succinamidohexanoyl)-aminoallyldeoxy-uridine 5'-triphosphate (PBA-XX-dUTP)

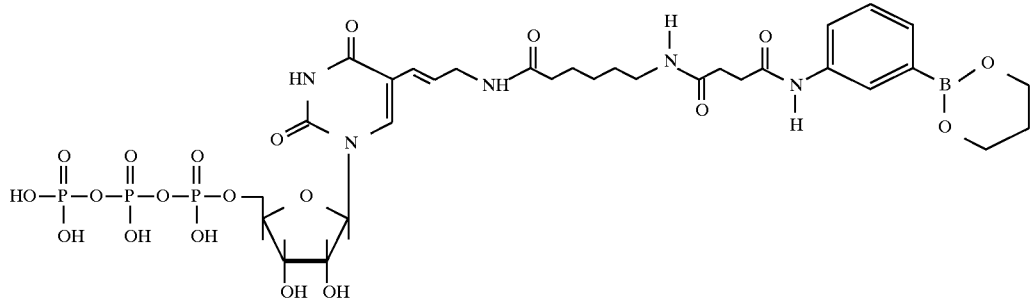

5-AA-dUTP (475 mL of stock solution in water, about 51 μmoles) was mixed with 1M aqueous sodium bicarbonate, pH about 8.5 (100 mL), and the solution was chilled in an ice/water bath. PBA-XX-NHS (25 mg, 51 μmoles) in dry N,N-dimethylformamide (100 μL) was added and the well-mixed reaction was allowed to sit at room temperature for 1 hour, then at 4° C. overnight. The product was isolated by reverse phase HPLC, using an Applied Biosystems/Brownlee Aquapore Butyl column, 220×10 mm, and a gradient of methanol in 0.1M triethylammonium acetate buffer, pH 6.5, over 20 minutes. The flow rate was 4.0 mL/minute. Absorbance was monitored at 260 nm. A 0.1 mL aliquot of the reaction mixture was injected for each run. Two major peaks were observed; the peak at about 18 minutes contained the desired product and was collected. The product fractions were combined and concentrated to about 0.5 mL. Ice-cold acetone (6 mL) was added to the product solution, and a white precipitate formed. The mixture was chilled at −20° C. overnight. The precipitate was pelleted by centrifugation (3000 rpm, 20 minutes, 4° C.). The supernatant was decanted and the pellet was dissolved in 0.5 mL of deionized water. The concentration of the product solution was calculated from the absorbance at 290 nm ($\epsilon \equiv 7000 M^{-1}\ cm^{-1}$). The yield was about 50%. This stock solution was stored frozen. $\lambda_{max}$: 251, 290 nm; $\lambda_{min}$: 271 nm (water). HPLC: Retention time of product, 20.4±0.1 minutes using the column, flow rate, buffers/solvents and detection as above. The gradient used was 100% A/0% B, 10 minutes, then to 50% A/50% B over 20 minutes.

PBA-X-dUTP can be prepared in a similar manner by substituting PBA-X-NHS (described above) for PBA-XX-NHS in the above reaction.

EXAMPLE 2

This example provides alternative methods for the preparation of modified polynucleotides using PCR with PBA-XX-dUTP; nick-translation with $NH_2$-dATP followed by reaction with an NHS-activated PBA group; and incorporation of PBA-XX-dUTP into oligonucleotides using random primed labeling, nick translation and terminal transfer tailing.

2.1 PCR Reaction

The protocol for the PCR reaction was a modification of the polymerase chain reaction described by Saiki, et al., Science 239:487–494 (1988). PCR primers (21mers) for the amplification of lambda DNA sequence 6371–7172, were synthesized with either a 5'-biotin label, three or four 5'-PBA labels, or no label. PBA was incorporated into an 801 bp product by polymerase insertion of PBA-XX-dUTP or by extension of PBA-labeled primer.

Figure 18:
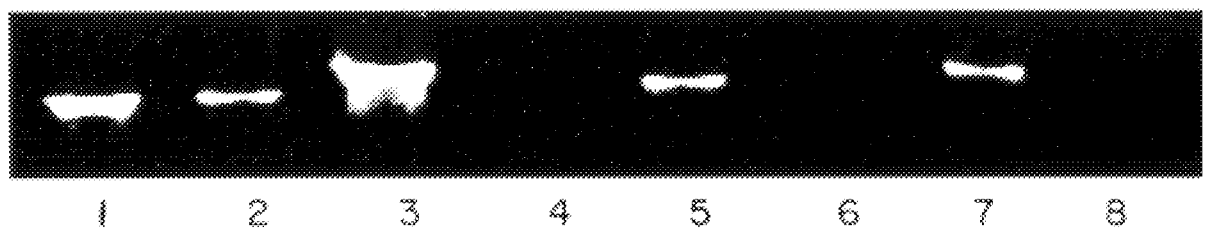
FIG. 18 is a gel which demonstrates the incorporation of PBA-XX-dUTP into a polynucleotide using PCR.

A standard PCR reaction for the incorporation of PBA-XX-dUTP was set up as follows: Lambda DNA was suspended (167 ng/mL) in 1XPCR buffer (Perkin Elmer, Foster City, Calif., U.S.A.), 1.5 mM $MgCl_2$, 200 μM dATP, 200 μM dCTP, 200 μM dGTP, 200 μM PBA-XX-dUTP, 1 μM biotin-6371 primer, 1 μM 7172-primer and 8.3 U/mL Taq DNA polymerase (Perkin Elmer). The PCR reaction mixture was placed in a thermocycler (Perkin Elmer) programmed with an initial 1–7 minute denaturation cycle (92° C.), followed by 30–35 cycles of denaturation (10 sec, 95° C.), annealing (20 sec, 62° C.), and extension (30 sec, 72° C.). After a final extension of 5 minutes (72° C.), the PCR reaction was held at 4° C. Approximately 50–100 ng of amplified product (801 bp) were produced. The PCR samples described above were mixed with DHBHA-Sepharose for 15 min at room temperature. The eluants from the DHBHA-Sepharose were compared to the starting PCR sample by electrophoresis on a 1% agarose, 10 μg/mL ethidium bromide, 50 mM Tris, 100 mM borate, 2 mM EDTA, pH 8.3 gel (see FIG. 18). The control PCR product (lane 1) did not bind substantially to the DHBHA-Sepharose (lane 2), while the PBA-XX-dUTP containing PCR products were bound quantitatively (lanes 4, 6 and 8) compared to the starting samples (lanes 3, 5 and 7, respectively).

Figure 19:
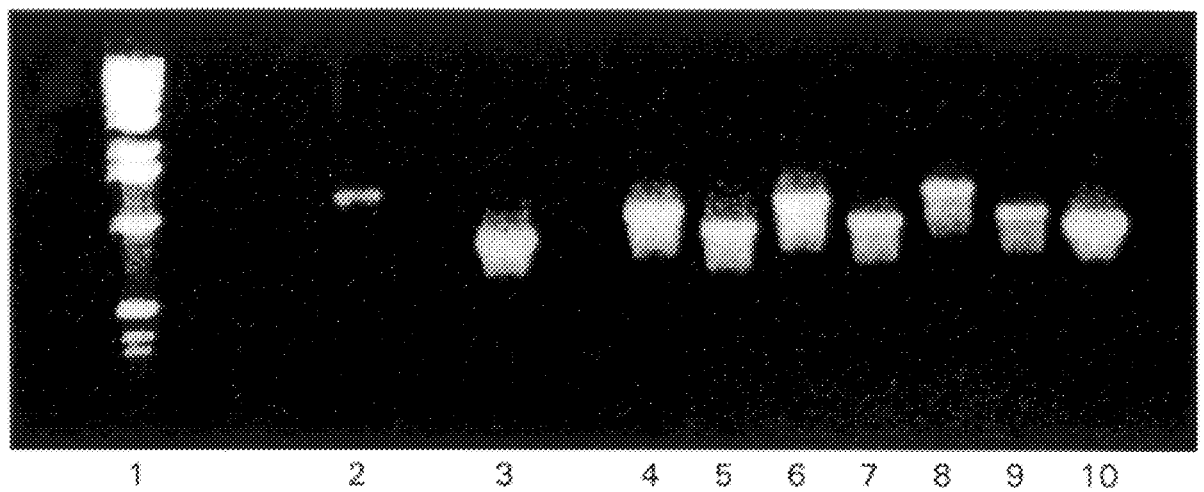
FIG. 19 is a gel which demonstrates the incorporation of PBA-XX-dUTP into a polynucleotide using random primed labeling and a PBA-labeled primer.

A standard PCR reaction for the extension of a PBA-labeled primer was set up as follows: Lambda DNA was suspended (167 ng/mL) in 1XPCR buffer (Perkin Elmer), 1.5 mM $MgCl_2$, 200 µM dATP, 200 µM dCTP, 200 µM dGTP, 200 µM dTTP, 1 µM biotin-6371 primer, 1 µM PBA-labeled 7172-primer, and 8.3 U/mL Taq DNA polymerase (Perkin Elmer). The PCR reaction mixture was placed in a thermocycler (Perkin Elmer) programmed with a 1 minute denaturation cycle (92° C.), followed by 30–35 cycles of denaturation (10 sec, 95° C.), annealing (20 sec, 62° C.), and extension (30 sec, 72° C.). After a final extension of 5 minutes (72° C.), the PCR reaction was held at 4° C. Approximately 200–400 ng of amplified product (801 bp) were produced, with no apparent retarding of mobility relative to unmodified PCR product on a 1% agarose, 50 mM Tris, 100 mM borate, 2 mM EDTA, pH 8.3 gel. FIG. 19 is a gel which compares PBA-labeled probes prepared by the alternative methods. In lane 1 is a standard 1 Kb ladder. Lane 2 is the product of PBA-XX-dUTP insertion into an 801 bp product. Lanes 3–9 contain products prepared by insertion reactions using mixtures of PBA-XX-dUTP and dTTP. Lane 10 is the product prepared by extension of a PBA-labeled primer.

2.2 Preparation of PBA-labeled Probe from $NH_2$-dATP Labeled Nucleic Acid

A nick translation reaction, a modification of the reaction described by Rigby, et al., *Journal of Molecular Biology* 113:237–251 (1977), was performed with N6-(6-aminohexyl)-dATP. One microgram of linear pBR322 DNA was suspended in 0.1 mM N6-(6-aminohexyl)-dATP (Gibco BRL, Gaithersburg, Md., U.S.A.), 0.125 mM dCTP, 0.125 mM dGTP, 0.125 mM dTTP, 1× buffer (Boehringer Mannheim, Indianapolis, Ind., U.S.A.), and ¹⁄₁₀ volume DNAaseI/DNA polymerase mix (Boehringer Mannheim). The reaction was incubated for 90 min at 15° C. and stopped by the addition of EDTA (50 mM). The amine-labeled DNA was precipitated by adding tRNA carrier (10 µg), one-tenth volume 4M LiCl, and 2.6 volumes of ethanol (10–20 min, –20° C.). After centrifugation for 15 min at 14,000 rpm (5° C.), the supernatant was decanted and the pellet was washed briefly in 70% ethanol (5° C.). The pellet was dried briefly, suspended in 30–40 µL of deionized $H_2O$ and adjusted to 7 mg/mL NHS-PBA, 0.36M $NaHCO_3$, 35% dimethyl formamide. After one hour at room temperature, a portion of the NHS-ester reacted DNA was precipitated by LiCl/ethanol precipitation. The resulting DNA pellet was suspended in a small volume of deionized $H_2O$. The purified or the crude NHS-reacted DNA was used in hybridizations to pBR322 DNA immobilized on a nylon membrane.

2.3 Preparation of PBA-labeled Probes

(a) Random Prime Labeling

Figure 20:
FIG. 20 is a gel which shows the random primed labeling incorporation of PBA-XX-dUTP and capture by DHBHA-Sepharose.

The random prime labeling reaction was a modification of Feinberg, et al., *Anal. Biochem.* 132:6–13 (1983), using PBA-XX-dUTP in place of dTTP. One microgram of DNA was denatured (100° C., 10 min). The DNA was quick chilled in a dry ice/ethanol bath. Two µL of 10× hexanucleotide mix (Boehringher Mannheim) and 2 µL of 10× dNTP labeling mix (1 mM dATP, 1 mM dCTP, 1 mM dGTP, 1 mM PBA-XX-dUTP) were added. The mixture was thawed and 1 µL of Klenow was added. The sample was incubated (37° C.) for 2–16 h and the reaction was stopped by the addition of EDTA (50 mM). Incorporation of PBA-XX-dUTP was verified by capture of the probe on DHBHA-Sepharose, demonstrated by electrophoresis of the eluants on a 1% agarose, 10 µg/mL ethidium bromide, 50 mM Tris, 100 mM borate, 2 mM EDTA, pH 8.3 gel (see FIG. 20). DNA labeled with dTTP (lane 1) was not captured by DHBHA-Sepharose (lane 2). However, DNA labeld with PBA-XX-dUTP (lane 3) was quantitatively captured by DHBHA-Sepharose (lane 4).

(b) Terminal Deoxynucleotidyl Transferase

The terminal transferase reaction was a modification of the reactions described by Abhay, et. al., *Anal. Biochem.* 169:376–382 (1988), using PBA-XX-dUTP diluted into dTTP.

Figure 21:
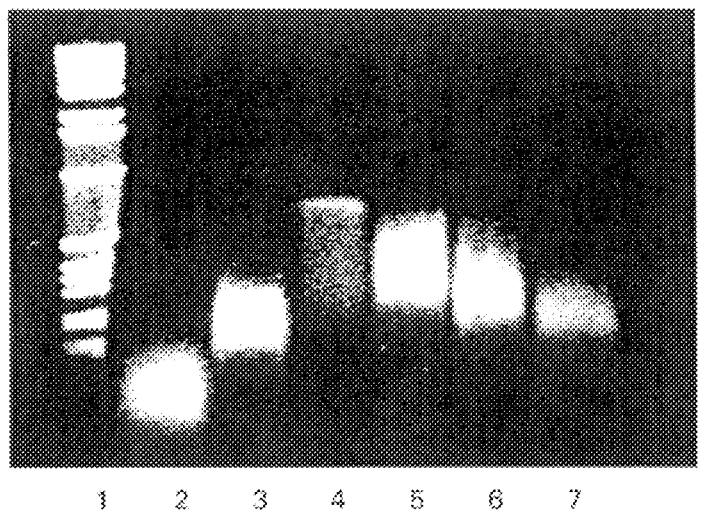
FIG. 21 is a gel which shows the terminal transferase incorporation of PBA-XX-dUTP into a 21-mer oligonucleotide.

One microgram of polynucleotide was suspended in 2 mM dATP, 2 mM dCTP, 2 mM dGTP, and 2 mM PBA-XX-dUTP or 2 mM PBA-XX-dUTP+dTTP, 1.5 mM $COCl_2$ 1× TdT buffer (Boehringher Mannheim), and 25 U terminal deoxynucleotidyl transferase. The reaction was incubated at 37° C. for 1–16 h and stopped by the addition of EDTA (50 mM). Incorporation was verified by capture of probe on DHBHA-Sepharose (not shown) or by mobility shift on a 1% agarose, 10 µg/mL ethidium bromide, 50 mM Tris, 100 mM borate, 2 mM EDTA, pH 8.3 gel (see FIG. 21). The oligonucleotide (lane 2) was tailed with dTTP (lane 3) or dilutions of PBA-XX-dUTP in dTTP (lanes 4–7). The presence of PBA-XX-dUTP retarded the mobility of the tailed oligonucleotide (lanes 4–7) relative to the dTTP tailed oligonucleotide (lane 3).

(c) Nick-translation

The nick translation reaction was a modification of the reaction described by Rigby, et al., *J. Mol. Biol.* 113:237–251 (1977), using PBA-XX-dUTP in place of dTTP. One microgram of DNA was suspended in 0.2 mM dATP, 0.2 mM dCTP, 0.2 mM dGTP, 0.2 mM PBA-XX-dUTP, 1× buffer (Boehringher Mannheim), and ¹⁄₁₀ volume DNAaseI/DNA polymerase mix (Boehringer Mannheim). The reaction was incubated for 90 min (15° C.) and stopped by the addition of EDTA (50 mM). Incorporation was verified by capture of probe on DHBHA Sepharose.

EXAMPLE 3

This example illustrates the preparation of magnetic particles having attached boronic acid binding moieties (or streptavidin) which are useful in the capture/detection methods described below. Additionally, the preparation of a coating protein having an attached boronic acid complexing moiety is also described. These coating proteins are also useful in purification methods as well as probe capture in microtiter plates.

3.1 Preparation of SHA- and SA-magnetic Particles

(a) Streptavidin-M280 Bead Preparation

Dynal M280 unmodified beads (Oslo Norway, product 142.10; lot 3490; 100 mL) were concentrated to 40 mL in a 50 mL conical tube using a rare earth alloy magnet (Dynal, Oslo Norway). The beads were washed three times with water, and then dehydrated into $CH_3CN$ (EM Science, Gibbstown, N.J.) by incubating sequentially for five minutes in 40 mL of 25, 50, and 75% aqueous $CH_3CN$. The beads were then washed three times with $CH_3CN$, and once with dry dioxane (Aldrich Chemical Co., Milwaukee, Wis.). The beads were suspended in 40 mL dioxane containing 50 mg/mL of 1,1'-carbonyldiimidazole (Aldrich Chemical Co., Milwaukee, Wis.) and rotated for one hour at room temperature. The beads were washed three times with $CH_3CN$, and suspended in 5 mL of 10 mg/mL streptavidin (Prozyme, San Leandro, Calif., U.S.A.) in 0.1M $NaHCO_3$. A 5 mL aliquot of 1M $NaHCO_3$ was added and the suspension was rotated for 5 hours at room temperature.

The beads were washed two times with 0.05% Tween 20® (polyoxyethylenesorbitan monolaurate, from Sigma Chemical Co., St. Louis, Mo., U.S.A.) in 0.1M $NaHCO_3$, then extensively with 0.1M $NaHCO_3$, and suspended in 45 mL of 0.1M $NaHCO_3$. The final suspension was stored at 4° C.

(b) SHA-M280 Bead Preparation

Dynal M280 beads (142.10; lot 3490; 100 mL) were concentrated and washed 3 times with water and dehydrated into $CH_3CN$ as above. The beads were washed three times with 10 mL of $CH_3CN$, once with 10 mL $CH_2Cl_2$ (Aldrich Chemical Co., Milwaukee, Wis.), and suspended in 18 mL $CH_2Cl_2$ in a 50 mL conical tube. 2 mL DMSO (Aldrich Chemical Co., Milwaukee, Wis.) were added, and the beads chilled five minutes in a dry ice/isopropanol bath. Four 200 ul aliquots of oxalyl chloride were added (Aldrich Chemical Co., Milwaukee, Wis.), and the reaction mixed occasionally during ten minutes in the dry ice bath. Triethylamine (Aldrich Chemical Co., Milwaukee, Wis.; 1000 $\mu$L) was added, and the reaction mixed occasionally during five minutes in the ice bath and then five minutes at room temperature. The beads were washed three times with $CH_3CN$, and rehydrated by reversing the dehydration procedure above, and washed once with water. The beads were then suspended in 36.4 mg SHA hydrazide (SHA-X-NH-NH2, lot rk02.43, fw=346.8, 59 $\mu$moles) dissolved in 400 $\mu$L DMSO and diluted in 20 mL of 0.1M NaOAc+1M NaCl pH 5.5. The bead reaction was rotated overnight at room temperature and washed extensively with water. The beads were suspended in 45 mL of water and stored in 5 mL aliquots at 4° C.

(c) SHA-M450 Bead Preparation

Dynal M450 beads (Dynal, Oslo Norway, 10 mL) were washed three times with water and dehydrated into $CH_3CN$ as described above. The beads were washed three times with 10 mL of $CH_3CN$, once with 10 mL of $CH_2Cl_2$, and suspended in 9 mL of $CH_2Cl_2$ plus 1 mL of DMSO. The were beads transferred to a 50 mL conical tube, and chilled for five minutes in a dry ice/isopropanol bath. Two 200 $\mu$L aliquots of oxalyl chloride were added and the reaction was mixed occasionally during 10 minutes in the ice bath. Triethylamine (500 $\mu$L) was added and the reaction was mixed occasionally during 5 minutes in the ice bath and then 5 minutes at room temperature. $CH_3CN$ (10 mL) was added to facilitate removal of the reaction mixture from the beads with a magnet. The beads were washed three times with $CH_3CN$ and rehydrated into water by reversing the dehydration procedure. The beads were washed three times water, and suspended in 18.5 mg SHA-X-NHNH$_2$ dissolved in 125 $\mu$L of DMSO and diluted in 5 mL of 0.1M NaOAc+ 0.1M NaCl, pH 5.5. The bead reaction was rotated over night at room temperature, washed six times with water, and suspended in 10 mL of water. The beads were stored at 4° C.

3.2 Preparation of SHA-plate Coating Protein

(a) SHA-Antibody for Plate Coating

One vial of goat anti-mouse polyclonal antibody (Rockland, Gilbertsville, Pa., product 210-1103) was dissolved in 5 mL of 0.1M $NaHCO_3$ to produce a solution of 8.8 mg/mL as determined spectrophotometrically assuming 1 mg/mL antibody has an absorbance at 280 nm of 1.4 in a 1 cm cuvette. Two mL of the antibody solution, assumed to contain 118 nmoles of antibody, was conjugated with 2,350 nmoles of SA(OMe)-X-NHS (rk01.222; fw=378), which was prepared by dissolving 1.6 mg of the NHS ester in 145 $\mu$L DMSO, and adding 100 $\mu$L of the solution to the antibody for one hour at room temperature.

The pH of the conjugation reaction was adjusted to 9.6 with 5 $\mu$L of 10N NaOH, and 2.1 mL of 2M $NH_2OH$, pH 10 were added. The reaction was incubated at room temperature for 3 days, and desalted on a 2.5×8 cm G-25 (Sigma Chemical Co., St. Louis, Mo.) in 50 mM $NaHCO_3$. The protein fraction was collected and had a volume of 12 mL. The UV spectrum of the desalted conjugate was measured on a Hewlett Packard 8453 diode array spectrophotometer. The concentration of the conjugate was estimated by subtracting the $A_{320}$ from the $A_{280}$ to estimate the $A_{280}$ from the antibody component of the conjugate. The conjugate concentration was estimated to be 1.75 mg/mL. The conjugate was stored at 4° C.

EXAMPLE 4

This example illustrates the capture/detection of a polynucleotide in which one strand on the captured duplex is PBA-labeled and the complementary strand has an attached biotin.

4.1 Detection of PBA-labeled PCR Product Bound to SHA-magnetic Particles

PBA-labeled PCR product (0.02 $\mu$L–5 $\mu$L) was diluted into 25–100 $\mu$L of 1.5N NaCl, 150 mM sodium citrate, pH 7 and added to a polypropylene microtiter plate well containing SHA-magnetic particles (10–50 $\mu$L). The particles and PCR product were mixed well and the binding occurred at room temperature (30–60 min). The magnetic particles were drawn to a magnetic plate and washed five times in 150 mM NaCl, 20 mM Tris-HCl, 0.02% Tween 20®, pH 8. One hundred microliters of streptavidin alkaline-phosphatase (0.2 U/mL in 1 mg/mL BSA, NaCl, Tris-HCl, pH 8: Boehringher Mannheim, Indianapolis, Ind., U.S.A.) or streptavidin-horseradish peroxidase (0.1 U/mL in 1 mg/mL BSA, NaCl, Tris-HCl, pH 8, Boehringher Mannheim) were added and mixed well with the magnetic particles. After 30 min (room temperature) the magnetic particles were drawn to a magnetic plate and washed 5–7 times in 150 mM NaCl, 20 mM Tris-HCl, 0.02% Tween 20®, pH 8. Substrate was added for alkaline phosphatase (1 mg/mL paranitrophenylphosphate in 1M diethanolamine, 2 mM $MgCl_2$, 0.2 mM $ZnCl_2$, pH 10.4) or horseradish peroxidase (ABTS 1-Step™ Pierce Chemical Co.). Substrate development (37° C.) occurred for 10–60 min. One microliter or less of PCR product ($\geq$50 pg) could be detected.

4.2 Detection of PBA-labeled PCR Product Bound to SHA-coated Microtiter Plates Polystyrene microtiter plates (Falcon, Becton Dickinson, Baltimore, Md., U.S.A.) were coated by filling wells with 200 μL of SHA-plate coating protein (30 μL/mL in 0.1M NaHCO$_3$, pH 9.0) and incubated overnight (4° C.) or incubated for 60 min (37° C.). The plate was washed 5 times with 150 mM NaCl, 20 mM Tris-HCl, 0.02% Tween 20®, pH 8 and backcoated with BSA (5 mg/mL in 0.2M NaHCO$_3$ pH 9.0) for 1.5 h (RT). The plate was washed 5 times with 150 mM NaCl, 20 mM Tris-HCl, 0.02% Tween 20®, pH 8. PBA-labeled PCR product (0.02 μL–5 μL was diluted into 25–100 μL of 1.5N NaCl, 150 mM sodium citrate, pH 7, was added to the SHA coated microtiter plate, and bound (RT; 30–60 min). The plate was washed five times in 150 mM NaCl, 20 mM Tris-HCl, 0.02% Tween 20®, pH 8. One hundred microliters of streptavidin alkaline-phosphatase (0.2 U/mL in 1 mg/mL BSA, NaCl, Tris-HCl, pH 8; Boehringher Mannheim) or strepavidin-horseradish peroxidase (0.1 U/mL in 1 mg/mL BSA, NaCl, Tris-HCl, pH 8, Boehringher Mannheim) were added. After 30 min (room temperature) the plate was washed 5–7 times in 150 mM NaCl, 20 mM Tris-HCl, 0.02% Tween 20°, pH 8. Substrate was added for alkaline phosphatase (1 mg/mL para-nitrophenyl phosphate in 1M diethanolamine, 2 mM MgCl$_2$, 0.2 mM ZnCl$_2$, pH 10.4) or horseradish peroxidase (ABTS I-StepT™, Pierce Chemical Co.). Substrate development (37° C.) occurs for 10–60 min. One microliter or less of PCR product (≧1.5 ng) could be detected.

EXAMPLE 5

This example illustrates the detection of PBA-labeled nucleic acid with SHA-labeled enzymes.

5.1 DHBHA Conjugation of Alkaline Phosphatase

One milliliter of alkaline phosphatase (6 mg/mL, Sigma, P-6774; from bovine intestine) was dialyzed against one liter of 0.1M NaHCO$_3$, and conjugated with 714 nmoles of DHBA(OMe)-X-NHS (10.5 μL of 68 mM in DMF) for two hours on ice. The methyl ester of the conjugate was converted to a hydroxamic acid by the adding one milliliter of 2M NH$_2$OH pH 10, and incubating the mixture at 4° C. for six days. The NH$_2$OH reaction mixture was then dialyzed against 0.1M NaHCO$_3$ and stored at 4° C.

5.2 SHA Conjugation of Alkaline Phosphatase

One milliliter of alkaline phosphatase (6.9 mg/mL, Sigma, P-6774; from bovine intestine) was dialyzed against one liter of 0.1M NaHCO$_3$, and conjugated with 668 nmoles of SA(OMe)-X-NHS (11.7 μL of 57 mM in DMF) for two hours on ice. The methyl ester of the conjugate was converted to a hydroxamic acid by adding one milliliter of 2M NH$_2$OH pH 10, adjusting the pH to 10 with 1N NaOH, and incubating the mixture at 4° C. for seven days. The NH$_2$OH reaction mixture was then dialyzed against 0.1M NaHCO$_3$ and stored at 4° C.

5.3 Detection of PBA-labeled Polynucleotide Hybrids Bound to Streptavidin-magnetic Beads with SHA-enzymes Polynucleotide PBA-7172 and biotin-complement 6371 were hybridized to opposite ends of a complementary 42mer in 1.5N NaCl, 150 mM sodium citrate, pH 7 for 10 min (RT) and cooled. The hybrid sandwich was added to a polypropylene microtiter plate well containing SHA-M450 magnetic particles (10–50 μL). The particles and hybrid sandwich were mixed well and the binding occurred at room temperature or 45° C. (30–60 min). The magnetic particles were drawn to a magnetic plate and washed five times in 150 mM NaCl, 20 mM Tris-HCl, 0.02% Tween 20®, pH 8. One hundred microliters of SHA-alkaline-phosphatase (1 μg/mL in 1 mg/mL BSA, NaCl, Tris-HCl, pH 8; Boehringher Mannheim) or SHA-horseradish peroxidase (1 μg/mL in 1 mg/mL BSA, NaCl, Tris-HCl, pH 8, Boehringher Mannheim) were added and mixed well with the magnetic particles. After 30 min (room temperature) the magnetic particles were drawn to a magnetic plate and washed 5–7 times in 150 mM NaCl, 20 mM Tris-HCl, 0.02% Tween 20®, pH 8. Substrate was added for alkaline phosphatase (1 mg/mL para-nitrophenyl phosphate in 1M diethanolamine; 2 mM MgCl$_2$, 0.2 mM ZnCl$_2$, pH 10.4) or horseradish peroxidase (ABTS 1-Step™, Pierce Chemical Co.). Substrate development (37° C.) occurred for 10–60 min. Forty-five picograms or greater of 42mer could be detected.

5.4 Detection of PBA-labeled Polynucleotide Hybrids Bound to Streptavidin-coated Microtiter Plates Polystyrene microtiter plates (Falcon, Becton Dickinson) were coated by filling wells with 200 μL of Streptavidin-Plus-(30 μg/mL in 0.1M NaHCO$_3$ pH 9.0; Prozyme) and incubated overnight (4° C.) or incubated 60 min (37° C.). The plate was washed 5 times with 150 mM NaCl, 20 mM Tris-HCl, 0.02% Tween 20®, pH 8 and backcoated with BSA (5 mg/mL in 0.2M NaHCO$_3$ pH 9.0) for 1.5 h (RT). The plate was washed 5 times with 150 mM NaCl, 20 mM Tris-HCl, 0.02% Tween 20®, pH 8. Polynucleotide PBA-7172 and biotin-complement 6371 were hybridized to a complementary 42mer in 1.5N NaCl, 150 mM sodium citrate, pH 7 for 10 min (RT) and cooled. The hybrid sandwich was added to the streptavidin-coated microtiter plate, and bound (RT; 30–60 min). The plate was washed five times in 150 mM NaCl, 20 mM Tris-HCl, 0.02% Tween 20®, pH 8. One hundred microliters of SHA-alkaline-phosphatase (1 μg/mL in 1 mg/mL BSA, NaCl, Tris-HCl, pH 8; Boehringher Mannheim) or SHA-horseradish peroxidase (1 μg/mL in 1 mg/mL BSA, NaCl, Tris-HCl, pH 8, Boehringher Mannheim) were added. After 30 min (RT) the plate was washed 5–7 times in 150 mM NaCl, 20 mM Tris-HCl, 0.02% Tween 20®, pH 8. Substrate was added for alkaline phosphatase (1 mg/mL para-nitrophenyl phosphate in 1M diethanolamine, 2 mM MgCl$_2$, 0.2 mM ZnCl$_2$, pH 10.4) or horseradish peroxidase (ABTS 1-Step™, Pierce Chemical Co.). Substrate development (37° C.) occurred for 10–60 min.

5.5 Detection of PBA-probe-SHA-alkaline Phosphatase Hybridized to Nucleic Acid Immobilized on Membranes PCR product (801 bp) or pBR322 DNA was denatured by adding NaOH to 0.56N (10 min, RT). The sample was mixed with an equal volume of 2M ammonium acetate, applied to a Nytran membrane (Schleicher and Scheull), and baked at 80° C. for 1–24 h or UV-irradiated for 60 sec. The membrane was wetted in 150 mM NaCl, 20 mM Tris-HCl, 0.02% Tween 20®, pH 8 and blocked in a blocking solution (Boehringher Mannheim) for 1 h (RT) or overnight (4° C.). The blocking solution was removed.

Fifty nanograms of PBA-oligo or denatured PBA-labeled probe were mixed with 5.3–26.5 μg of SHA-alkaline phosphatase and incubated (10 min, RT). Conjugate diluent (0.5 mg/mL BSA in 150 mM NaCl, 20 mM Tris-HCl, 0.02% Tween 20®, pH 8) was added to the probe-enzyme mixture to 1 mL (1 min, RT). The mixture was added to the blocked membrane that was in 9 mL of hybridization solution (1M NaCl, 20 mM Tris-HCl pH 7.5, 1 mM EDTA, 0.05% Tween20). The hybridization was performed for one hr to overnight (RT-37° C.). The membrane was washed five-seven times in 150 mM NaCl, 20 mM Tris-HCl, 0.02% Tween 20®, pH 8 and substrate solution (103 mM nitro blue tetrazolium, 759 mM 5-bromo-4-chloro-3-indoyl-phosphate, 0.1M Tris-HCl pH 9.0., 0.1M NaCl, 50 mM $MgCl_2$) was added. Color development occurred in the dark for 1–16 h. As few as 4 pg of DNA could be detected, depending upon type of probe, concentration of probe, hybridization time, and substrate incubation time.

All publications, patents and patent applications mentioned in this specification are herein incorporated by reference into the specification to the same extent as if each individual publication, patent or patent application was specifically and individually indicated to be incorporated herein by reference.

The above description is illustrative and not restrictive. Many variations of the invention will become apparent to those of skill in the art upon review of this disclosure. The scope of the invention should, therefore, be determined not with reference to the above description, but instead should be determined with reference to the appended claims along with their full scope of equivalents.

What is claimed is:

1. A modified polynucleotide having the formula:

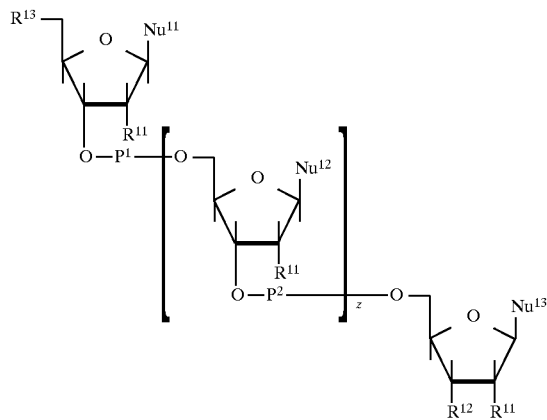

wherein
  z is an integer of from 1 to 1000;
  each $R^{11}$ is independently selected from the group consisting of —H and —OH;
  $R^{12}$ and $R^{13}$ are each members independently selected from the group consisting of hydroxyl, protected hydroxyl, monophosphate ester, diphosphate ester and triphosphate ester;
  each $P^1$ and $P^2$ is independently selected from the group consisting of —P(O)(OH)—, —P(O)($NH_2$)—, —P(S)(OH)—, —P(O)($CH_3$)—, and pharmaceutically acceptable salts thereof;
  each $Nu^{11}$, $Nu^{12}$ and $Nu^{13}$ is independently selected from the group consisting of

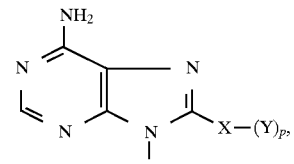

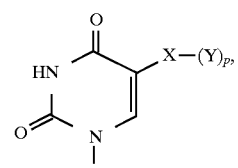

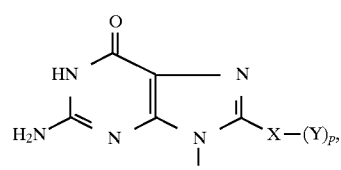

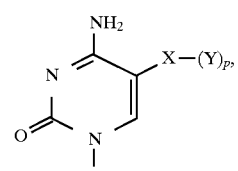

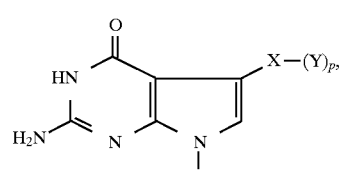

adenine, guanine, thymine and cytosine,
wherein
  X is a linking group comprising of from 7 to 30 carbon atoms, a portion of which is an aromatic ring; and
  Y is a member selected from the group consisting of —B(OH)$_2$, —B(OH)(OR) and —B(OR)(OR'), wherein R and R' are each independently lower alkyl groups having from one to six carbon atoms; and
  p is an integer of from 1 to 3;
with the proviso that at least one and no more than thirty of $Nu^{11}$, $Nu^{12}$ and $Nu^{13}$ are other than adenine, guanine, thymine or cytosine.

2. A modified polynucleotide in accordance with claim 1, wherein $R^{12}$ is hydroxyl and $R^{13}$ is a monophosphate ester.

3. A modified polynucleotide in accordance with claim 1, wherein z is an integer of from about 5 to about 100.

4. A modified polynucleotide in accordance with claim 1, wherein z is an integer of from about 10 to about 30.

5. A modified polynucleotide in accordance with claim 1, wherein one of $Nu^{11}$, $Nu^{12}$ or $Nu^{13}$ is a member selected from the group consisting of

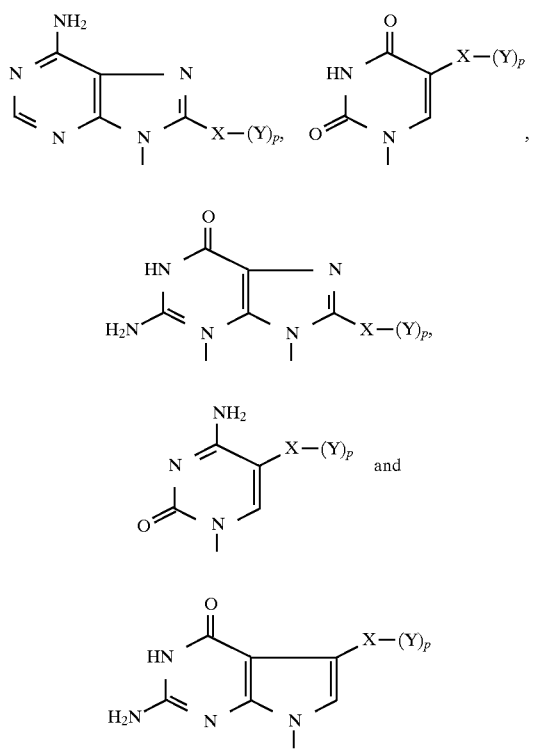
wherein —X— and —(Y)$_p$ taken together comprise a radical selected from the group consisting of
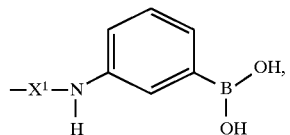
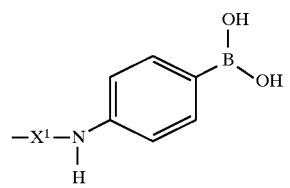
and
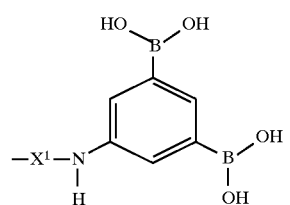
in which X$^1$ is a linking group fragment comprising of from 3 to 23 carbon atoms.
* * * * *

UNITED STATES PATENT AND TRADEMARK OFFICE
CERTIFICATE OF CORRECTION

PATENT NO. : 5,831,045
DATED : November 3, 1998
INVENTOR(S) : Mark L. Stolowitz, *et al.*

It is certified that error appears in the above-identified patent and that said Letters Patent is hereby corrected as shown below:

On the title page: Item [73] the assignee's name is spelled incorrectly. It should read:

Assignee: Prolinx, Incorporated, Bothell, Wash.

Signed and Sealed this

Second Day of March, 1999

Attest:

Q. TODD DICKINSON

*Attesting Officer*     *Acting Commissioner of Patents and Trademarks*